(12) United States Patent
Lee

(10) Patent No.: US 6,692,777 B2
(45) Date of Patent: Feb. 17, 2004

(54) PHARMACEUTICAL COMPOSITION FOR THE TREATMENT OF DIABETES MELLITUS

(76) Inventor: Seung Young Lee, A-101, Geoboong Heiz Villa, 77-5, Yeonhee-dong, Seodaemun-gu, Seoul (KR), 120-110

( * ) Notice: Subject to any disclaimer, the term of this patent is extended or adjusted under 35 U.S.C. 154(b) by 187 days.

(21) Appl. No.: 10/050,933

(22) Filed: Jan. 22, 2002

(65) Prior Publication Data

US 2002/0197334 A1 Dec. 26, 2002

(30) Foreign Application Priority Data

Jan. 22, 2001 (KR) .................................... 2001-0003624
Oct. 19, 2001 (KR) .................................... 2001-0066825

(51) Int. Cl.$^7$ .............................................. A61K 35/78
(52) U.S. Cl. ....................................................... 424/725
(58) Field of Search .......................................... 424/725

(56) References Cited

FOREIGN PATENT DOCUMENTS

KR    2001-0029771    4/2001

Primary Examiner—Jean C. Witz
(74) Attorney, Agent, or Firm—Jacobson Holman PLLC

(57) ABSTRACT

This invention relates to a pharmaceutical composition containing herbal ingredients for the treatment of diabetes mellitus and more particularly, to the antidiabetic composition comprising 1) 15 herbal ingredients (i.e., Shinseng Radix, Coptis Rhizoma, Ligustri Fructus Semen, Salix spp. Cortex, *Rhei coreani* Rhizoma, Anemarrhena Rhizoma, Salviae Radix, Scrophulariae Radix, Lycii Cortex Radicis, Reynoutriae Radix, Platycodi Radix, Astragali Radix, Puerariae Radix, Atractylis Rhizoma, and *Morus alba* Radix Cortex), 2) vitamins such as $B_1$ and $B_6$, and 3) zinc, manganese, chromium, germanium as inorganic materials.

The antidiabetic herbal composition of this invention for the prevention and treatment of diabetes serves to lower the glucose level in diabetic patients and prevent the destruction of beta-cell in the pancreas, while increasing insulin secretion based on the mechanism of recovering the function of damaged beta-cell. Further, the antidiabetic herbal composition of this invention is quite effective in the treatment of insulin-dependent (type I) diabetes and non-insulin-dependent (type II) diabetes, since it shows the constant therapeutic effect due to better stability of therapeutic effect among individual patients.

2 Claims, 8 Drawing Sheets

PHARMACEUTICAL COMPOSITION FOR THE TREATMENT OF DIABETES MELLITUS

BACKGROUND OF THE INVENTION

Field of the Invention

This invention relates to a pharmaceutical composition containing herbal ingredients for the treatment of diabetes mellitus and more particularly, to the antidiabetic composition comprising 1) 15 herbal ingredients (i.e., Shinseng Radix, Coptis Rhizoma, Ligustri Fructus Semen, Salix spp. Cortex, *Rhei coreani* Rhizoma, Anemarrhena Rhizoma, Salviae Radix, Scrophulariae Radix, Lycii Cortex Radicis, Reynoutriae Radix, Platycodi Radix, Astragali Radix, Puerariae Radix, Atractylis Rhizoma, and *Morus alba* Radix Cortex), 2) vitamins such as Bi and B6, and 3) zinc, manganese, chromium, germanium as inorganic materials.

The antidiabetic herbal composition of this invention for the prevention and treatment of diabetes serves to lower the glucose level in diabetic patients and prevent the destruction of beta-cell in the pancreas, while increasing insulin secretion based on the mechanism of recovering the function of damaged beta-cell. Further, the antidiabetic herbal composition of this invention is quite effective in the treatment of insulin-dependent (type I) diabetes and non-insulin-dependent (type II) diabetes, since it shows the constant therapeutic effect due to better stability of therapeutic effect among individual patients.

Diabetes with its complications is a disease showing a high mortality worldwide in line with other diseases such as cancer, cardiovascular disorders. The mortality of diabetes has persisted and there are many reports that the diabetic patients have a high risk of having some related complications in eye, kidney and heart.

The symptoms of diabetes may vary but its main three complaints are excessive water intake, excessive urination and excessive food intake. More specifically, the glucose level in the blood becomes abnormally high, causing excessive urination and constant thirst and hunger. The body's inability to store glucose causes weight loss.

There are two main types of diabetes mellitus such as insulin-dependent (type I) diabetes and non-insulin-dependent diabetes (type II). Insulin-dependent diabetes tends to cause severe symptoms such as diabetic ketoacidosis due to the severe insufficiency of insulin. In Europe and U.S.A., insulin-dependent diabetes accounts for about 5~10% in all diabetic patients, while it represents about 1~2% in Korea. Insulin-dependent diabetes is called "youth diabetes", since it appears in teenagers and youngsters in their twenties. The cause of insulin-dependent diabetes is associated with some gene factor such as HLA antigen (HLA, DR, DQ). Another environmental factors inducing insulin-dependent diabetes include viruses and some toxic materials that may affect the immune source as the surface antigen of beta-cell, insulin-secreting cell in the pancreas. The autoimmune mechanism has shown to be involved in the occurrence of diabetes, thus producing the auto-antibody against Langerhans island cell and insulin. Recently, efforts have been made to slow or prevent the occurrence of insulin-dependant diabetes by detecting the auto-antibody in an earlier stage.

The other main type, non-insulin-dependent diabetes, is usually of gradual onset and occurs in people over 40 years old. Unlike insulin-dependent diabetes, type II diabetes is called "adult diabetes" and its etiology has been unknown. Evidences have shown that non-insulin-dependent diabetes may be associated with genetic and environmental factors. In the case of non-insulin-dependent diabetes, it tends to heavily run in families and identical twins who has the genes responsible for the non-insulin-dependent diabetes by 90~100%. When both parents have diabetes, 58% of children may have diabetes; when one of the parents has diabetes, 27% of diabetes may occur in children; when both parents are normal, only 0.9% of diabetes may occur in children. The environmental factors responsible for diabetes include high-calorie food intake triggered by rapid economic growth in recent years, insufficient exercise, obesity, stress and drug overuse. The pathology of non-insulin-dependent diabetes may be associated with insufficient secretion of insulin and malfunction of insulin at target cell (insulin resistance) but the primary factor has yet to be elucidated.

The examples of oral glucose-lowering agents for the treatment of diabetes include sulfonylureas, biguanides and acarbose. The second-generation sulfonylureas have been frequently used, since its duration of action is short with a potent glucose-lowering effect in non-obese diabetic patients, while biguanides and acarbose are indicated for obese diabetic patients exceeding the normal body weight.

The marked difference among these anti-diabetic agents is that biguanides and acarbose has less incidence of hypoglycemia than sulfonylureas.

Special attention, especially in the elderly people, should be exercised when an injecTable form of insulin is administered, since hypoglycemia may occur and its use is quite inconvenient.

In addition to these drug medications, there are 158 traditional drugs including 153 oral drugs in Korea. It has been reported that about 73% of adult diabetic patients have experienced the traditional antidiabetics more than once.

The current research for antidiabetics has focused on the prevention and treatment of diabetes. In the case of insulin-dependent diabetes, some animal experiments using NOD mice model have been mainly performed for the prevention of insulitis and diabetes. The majority of antidiabetic approaches have been centered on the inhibition and modulation of immune response for preventing the destruction of beta-cell. Insulin-dependent diabetes, an autoimmune disease, is caused by abnormal potentiation of immune function. Diverse immunotherapies designed to prevent the destruction of beta-cell in the pancreas have been applied. Neonatal thymectomy can eliminate T-cell in NOD mice, which may contribute to the inhibition of diabetes. Evidences have shown that the elimination of T-cell and macrophage via appropriate modulation of antibody against T-cell may also prevent the occurrence of diabetes. Another studies have indicated that the use of various antioxidants that inhibits the formation and action of free radicals such as NO secreted from the immune cell may inhibit the occurrence of diabetes. These oxidants include nicotinamide, vitamin E, probucol, MDL29311 and U78518F.

Many studies have been actively conducted based on immunosuppressants but glucocorticoid and cyclophosphamide have failed to demonstrate their significant efficacy against diabetes. Another strategies using cyclosporin A, rapamycin and FK506 have been suggested, but its results are unclear. The use of immunosuppressants as antidiabetic drug has faced some problems associated with side effects such as secondary infection, renal and hepatic toxicities due to the excessive immune suppression, and their long-term use may induce cancer. The recent studies have shown that some immunomodulators, not immunosuppressants, for the prevention and treatment of diabetes may inhibit diabetes in NOD mice via modulation of cytokines such as IL-4 and -IL-10. Evidences have indicated that some immunomodulators such as OK-432, LZ-8, BCG, and CFA may contribute to the treatment of diabetes, but their mode of action have yet to be elucidated.

Currently, investigators have endeavored to develop a novel drug with less side effects for the treatment of both insulin-dependent and non-insulin dependent diabetes. It has been reported that oriental medicines have diverse therapeutic efficacy with less side effects in a traditional term. Some studies have demonstrated that oriental medicine-based regimens using many herbs singly or in combination have proven their superior efficacy in the treatment of diabetes, even in the treatment of both insulin-dependent and non-insulin dependent diabetes simultaneously.

SUMMARY OF THE INVENTION

In this context, the inventor has undertaken the intensive studies to develop a pharmaceutical composition for the treatment of both insulin-dependant and non-insulin-dependant diabetes simultaneously based on the mixture of various herbal ingredients with less side effects. For the treatment of insulin-dependant diabetes, a drug designed to prevent the destruction of beta-cell in the pancreas and to facilitate the secretion of insulin in beta-cell is essential. Thus, the challenging task was achieved in animal experiments using STZ and NOD mice. Further, the effective treatment of non-insulin-dependant diabetes could be achieved by the inhibition of the drastic increase of glucose level after food intake and alleviation of insulin resistance in the peripheral tissues; in this case, KK-Ay mice were used and the inventor found that the herbal composition of this invention has a glucose-lowering effect with stability of the therapeutic effect among individuals, thus, this invention has been completed. Therefore, the object of this invention is to provide a novel herbal composition for the treatment of both insulin-dependant and non-insulin-dependant diabetes. This invention is explained in detail as set forth hereunder.

BRIEF DESCRIPTIONS OF THE DRAWINGS

FIG. 1 is a graph showing the results of glucose tolerance test in animal experiments using normal ICR mice. After being fasted for 24 hours, animals were administered intraperitoneally the herbal specimen of this invention at the dose of 267 mg/kg. 90 minutes after administration, glucose was orally administered to animals at the dose of 1 g/kg and changes in glucose level were measured at the time intervals.

Figure 6:
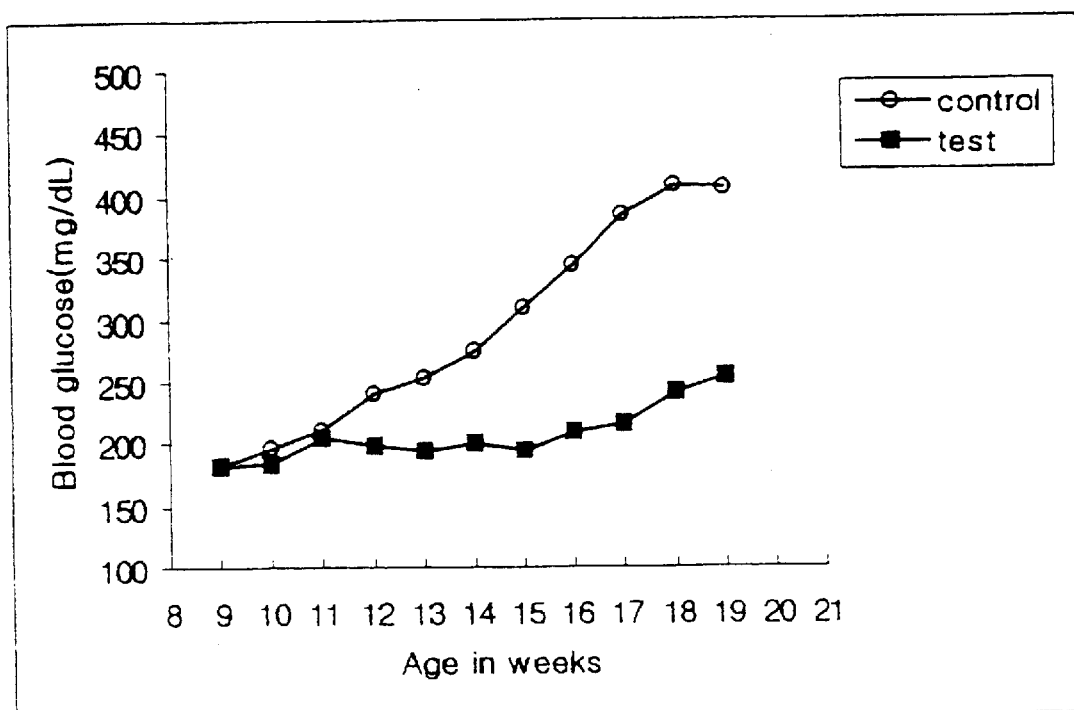
FIG. 6 is a graph showing the antidiabetic effect of the herbal composition of this invention in animal experiments using NOD mice. Animals ranging from 11 weeks to 20 weeks were administered intraperitoneally the herbal specimen of this invention at the dose of 267 mg/kg.

FIGS. 7a~7d are photographs of the pancreas separated from NOD mice in FIG. 6 where insulitis is tested pathologically.

DETAILED DESCRIPTION OF THE INVENTION

This invention relates to a pharmaceutical composition for the treatment of diabetes and more particularly, to the antidiabetic composition comprising 1) 15 herbal ingredients (i.e., Shinseng Radix, Coptis Rhizoma, Ligustri Fructus Semen, Salix spp. Cortex, *Rhei coreani* Rhizoma, Anemarrhena Rhizoma, Salviae Radix, Scrophulariae Radix, Lycii Cortex Radicis, Reynoutriae Radix, Platycodi Radix, Astragali Radix, Puerariae Radix, Atractylis Rhizoma, and *Morus alba* Radix Cortex), 2) vitamins such as $B_1$ and $B_6$, and 3) zinc, manganese, chromium, germanium as inorganic materials.

More specifically, the herbal composition of this invention for the treatment of diabetes comprises 1) 400~800 wt. part of Shiseng Radix, 1900~3400 wt. part of Coptis Rhizoma, 50~400 wt. part of Ligustri Fructus Semen, 170~1700 wt. part of Salix spp. Cortex, 50~600 wt. part of *Rhei coreani* Rhizoma, Rhizoma, 500~800 wt. part of Anemarrhena Rhizoma, 400~600 wt. part of Salviae Radix, 400~700 wt. part of Scrophulariae Radix, 500~800 wt. part of Lycii Cortex Radicis, 400~600 wt. part of Reynoutriae Radix, 300~500 wt. part of Platycodi Raidx, 900~1300 wt. part of Astragali Radix, 600~800 wt. part of Puerariae Radix, 600~800 wt. part of Atractylis Rhizoma, and 250~450 wt. part of *Morus alba* Radix Cortex, 2) in proportion to the total weight of the herbal composition, 0.5~4.0% of vitamin $B_1$ and 0.5~5.0% of vitamin $B_6$, including 3) 0.2~1.0% of zinc, 0.2~1.0% of manganese, 0.001~0.005% of chromium, and 0.5~4.0% of germanium as inorganic materials.

Further, this invention may comprises a total of 19 herbs including 500~800 wt. part of *Euonymus alatus*, 250~550 wt. part of Corni Fructus, 300~600 wt. part of Cassiae Semen, and 300~600 wt. part of Ophiopoigonis Tuber in addition to the above composition. Furthermore, this invention may comprises a total of 22 herbs including 100~200 wt. part of *Panax notoginsen*, 100~200 wt. part of *Panax quinquefolium* Radix, and 300~600 wt. part of Antractylis Rhizoma in addition to the above 19 herbs.

1) Shiseng Radix is a herbal medicine belonging to Araliaceae and is indicated for tonics, neurologic breakdown, general weakness, indigesion, vomiting and diarrhea as the "king of tonics". Glycosides contained in alcohol extract are believed to inhibit the glucose level and to be closely related to carbohydrate metabolism in animals.

2) Coptis Rhizoma is a herbal medicine belonging to Ranunculaceae and its active ingredients are berberine, palmitine, jateorrhizine, coptisine and worenine as stomachic and preparation for intestinal flora with bitter taste. The active ingredient berberine has an antimicrobial action that can inhibit the growth of intestinal bacteria. It is used in the treatment of gastric disturbance, hemorrhage, arteriosclerosis, inflammation, and mental anxiety in the oriental medicine.

3) Ligustri Fructus Semen is a dried fruit of Ligustrum Japonicum Thunberg which belongs to Oleaceae. It contains glycosides and syringin and is used as tonics.

4) Salix spp. Cortex which belongs to Saliaceae contains salicin and populin as salicylic acid glycosides. It has been used for a long time as antipyretics and analgesics. Its branch, trunk and leaf in the oriental medicine are used to treat fever, pain and athlete's foot. The herbal composition of this invention mainly employs Salix gilgiana instead of Salix spp. Cortex.

5) *Rhei coreani* Rhizoma belongs to Polygonaceae and its main ingredients are chrysophanic acid, emodin glycoside, resin, etc. It is used for diarrhea and relaxation in the oriental medicine. The different types of *Rhei coreani* Rhizoma include Rhei Rhizoma and *Rhei undulati* Rhizoma.

6) Anemarrhena Rhizoma which belongs to Liliaceae is a herbal medicine containing saponins (e.g., asphonin, sarasapogenin, markogenin) and flavonoid chimonin as active ingredients. It is used as analgesics and diuretics in the oriental medicine.

7) Salviae Radix which belongs to Ladiatae is a herbal medicine containing tanshinone as an active ingredient. It is used for tonics, menstrual disorder, women's disease (e.g., uterine hemorrhage) and stomach pain in the oriental medicine.

8) Scrophulariae Radix which belongs to Scrophulariaceae is a herbal medicine containing p-methoxycinnamic acid as an active ingredient. It is used as anti-inflammatory agent, analgesic, and painkiller in the oriental medicine.

9) Lycii Cortex Radicis is a root trunk of Lycium Chinense Miller which belongs to Solanaceae. It is used as anti-inflammatory agent, analgesic, and tonics for the treatment of pulmonary tuberculosis and diabetes in the oriental medicine.

10) Reynoutriae Radix is a dried root of Reynoutria elliptica Migo which belongs to Plygonaceae. It contains anthraquinone glycosides of polygonins. It is used for relaxant, diuretic, and menstrual disorder in the oriental medicine. This drug is decocted with Glycyrrhizae Radix for the treatment of tussis.

11) Platycodi Radix is a peel-stripped root of Platycodon grandiflorum which belongs to Campanulaceae or a dried plant as of the original shape. It contains saponins such as kikyo-saponin, platycodin, inulin, and phytosterol. It is widely used as expectorants in the oriental medicine.

12) Astragali Radix which belongs to Leguminosae is a herbal medicine and is indicated for weakness and dropsy as relaxant, tonic, anti-sweating agent, and diuretic as well as vasodilation and antihypertensive action. Recently, it is replaced by Shinseng Radix.

13) Puerariae Radix is a root of Pueraria thunb which belongs to Leguminosae, whose cork peel is removed and made in the form of fragment. It contains daidzin, puerarian, and starch. It is used as anti-sweating agent and antipyretic in the oriental medicine.

14) Atractylis Rhizoma is a dried root trunk of Atractylis lyrata Siebold et Zuccarini which belongs to Compositae. It contains atractylone as an essential oil. It is used as aromatic stomachic and diuretic in the oriental medicine.

15) *Morus alba* Radix Cortex is a root peel of *Morus alba* which belongs to Moraceae. Its extract contains pectin and amyrine as well as nozirimycin as antidiabetic.

Other additional herbal medicines, such as *Euonymus alatus*, Corni Fructus, Cassiae semen, Ophiopogonis Tuber, *Panax notoginsen, Panax quinquefolium* Radix, and Atractylis *Rhizoma alba* have been well recognized in the oriental medicine in Korea.

The antidiabetic composition of this invention may replace Coptis Rhizoma by Phellodendri Cortex or purified berberin hydrochloride. In addition, purified oleanolic acid may be used instead of Ligustri Fructus Semen, and purified or synthesized salicylic acid or acetyl salicylic acid and its salt may be also used instead of Salix spp. Cortex.

Further, the antidiabetic composition of this invention may use Rosa rogosa Radix or Araliae Cortex in addition to the aforementioned herbal medicines. Also, other different vitamins such as $B_2$, $B_{12}$ and C may be used in addition to water-soluble vitamins $B_1$ and $B_6$. Other inorganic materials such as calcium and potassium may also be used in addition to zinc, manganese, chromium, and germanium.

The antidiabetic composition of this invention may include pharmaceutically accepTable excipients to formulate the dosage forms of -Tablet or capsule in the commonly used method. The dose may be 5~3000 mg/kg as body weight/day, preferably by 101000 mg/kg as body weight/day. The antidiabetic composition of this invention may be administered 3~4 times daily at the dose of 2~4 capsules once 30 minutes before meals. The dosage may be adjusted depending on the condition of patients and the lowered glucose level. The maintenance dose is preferably 4~6 capsules daily.

The preparation examples and antidiabetic test results of herbal composition of this invention are attached herein.

PREPARATION EXAMPLE 1

Capsule Preparation (as 1,000 Capsules)

|  | Ingredients | Preparation example of capsule | | |
|---|---|---|---|---|
|  |  | Example 1 | Example 2 | Example 3 |
| Herbs | Shinseng Radix | 500 g | 450 g | 700 g |
|  | Coptis Rhizoma | 2,430 g | 1,950 g | 3,300 g |
|  | Ligustri Fructus Semen | 360 g | 70 g | 350 g |
|  | Salix spp. Cortex | 1,100 g | 200 g | 1,000 g |
|  | *Rhei Coreani* Rhizoma | 200 g | 60 g | 450 g |
|  | Anemarrhena Rhizoma | 660 g | 550 g | 750 g |
|  | Salviae Radix | 500 g | 440 g | 550 g |
|  | Scrophulariae Radix | 500 g | 420 g | 650 g |
|  | Lycii Cortex Radicis | 660 g | 530 g | 750 g |
|  | Reynoutriae Radix | 500 g | 400 g | 500 g |
|  | Platycodi Radix | 400 g | 360 g | 450 g |
|  | Astragali Radix | 1,020 g | 950 g | 1,200 g |
|  | Puerariae Radix | 660 g | 660 g | 700 g |
|  | Atractylis Rhizoma | 660 g | 640 g | 750 g |
|  | *Morus alba* Radix Cortex | 360 g | 300 g | 400 g |
|  | *Panax notoginsen* |  |  | 110 g |
|  | *Panax quinque-folium* Radix |  |  | 120 g |
|  | *Euonymus alatus* |  | 750 g | 550 g |
|  | Corni Fructus |  | 520 g | 300 g |
|  | Antractylis *Rizoma alba* |  |  | 300 g |
|  | Cassiae semen |  | 550 g | 320 g |
|  | Ophiopogonis Tuber |  | 560 g | 330 g |
|  | Sub-total | 381.795 g | 385.5 g | 421.0 g |
| Additives | Thiamine HCl | 3.0 g | 3.0 g | 3.0 g |
|  | Pyridoxine HCl | 4.0 g | 4.0 g | 4.0 g |
|  | Zinc sulfate | 3.2 g | 3.2 g | 3.2 g |
|  | Manganese sulfate | 4.0 g | 4.0 g | 4.0 g |
|  | Chrome chloride | 5.0 mg | 5.0 mg | 5.0 mg |
|  | Germanium | 4.0 g | 4.0 g | 4.0 g |

-continued

| | Ingredients | Preparation example of capsule | | |
|---|---|---|---|---|
| | | Example 1 | Example 2 | Example 3 |
| | (Ge-132) | | | |
| | Sub-total | 18.205 g | 18.205 g | 18.205 g |
| Capsule base | No. 0 capsule | 70 mg | 70 mg | 70 mg |
| | Weight of capsule preparation | 470 mg | 473.7 mg | 509.2 mg |

PREPARATION EXAMPLE 2

Tablet Preparation (as 1,000 Tablets)

| | | Preparation example of Tablet | | |
|---|---|---|---|---|
| | Ingredients | Example 1 | Example 2 | Example 3 |
| Herbs | Shinseng Radix | 500 g | 450 g | 700 g |
| | Coptis Rhizoma | 2,430 g | 1,950 g | 3,300 g |
| | Ligustri Fructus Semen | 360 g | 70 g | 350 g |
| | Salix spp. Cortex | 1,100 g | 200 g | 1000 g |
| | *Rhei Coreani* Rhizoma | 200 g | 60 g | 450 g |
| | Anemarrhena Rhizoma | 660 g | 550 g | 750 g |
| | Salviae Radix | 500 g | 440 g | 550 g |
| | Scrophulariae Radix | 500 g | 420 g | 650 g |
| | Lycii Cortex Radicis | 660 g | 530 g | 750 g |
| | Reynoutriae Radix | 500 g | 400 g | 500 g |
| | Platycodi Radix | 400 g | 360 g | 450 g |
| | Astragali Radix | 1,020 g | 950 g | 1,200 g |
| | Puerariae Radix | 660 g | 660 g | 700 g |
| | Atractylis Rhizoma | 660 g | 640 g | 750 g |
| | *Morus alba* Radix Cortex | 360 g | 300 g | 400 g |
| | *Panax notoginsen* | | | 110 g |
| | *Panax quinquefolium* Radix | | | 120 g |
| | *Euonymus alatus* | | 750 g | 550 g |
| | Corni Fructus | | 520 g | 300 g |
| | Antractylis Rizoma alba | | | 300 g |
| | Cassiae semen | | 550 g | 320 g |
| | Ophiopogonis Tuber | | 560 g | 330 g |
| | Sub-total | 381.795 g | 385.5 g | 421.0 g |
| Additives | Thiamine HCl | 3.0 g | 3.0 g | 3.0 g |
| | Pyridoxine HCl | 4.0 g | 4.0 g | 4.0 g |
| | Zinc sulfate | 3.2 g | 3.2 g | 3.2 g |
| | Manganese sulfate | 4.0 g | 4.0 g | 4.0 g |
| | Chrome chloride | 5.0 mg | 5.0 mg | 5.0 mg |
| | Germanium (Ge-132) | 4.0 g | 4.0 g | 4.0 g |
| | Sub-total | 18.205 g | 18.205 g | 18.205 g |
| Excipients | Non-crystal cellulose | 50 g | 50 g | 50 g |
| | Lactose | 22 g | 22 g | 22 g |
| | Silicone dioxide | 5.5 g | 5.5 g | 5.5 g |
| | PVP K30 | 8.0 g | 8.0 g | 8.0 g |
| Lubricant | Magnesium stearate | 16.0 g | 16.0 g | 16.0 g |
| Coating agent | HPMC 2910 | 10.0 g | 10.0 g | 10.0 g |
| | PEG 6000 | 8.0 g | 8.0 g | 8.0 g |
| | Titanium dioxide | 0.5 g | 0.5 g | 0.5 g |
| | Ethanol | 0.16 ml | 0.16 ml | 0.16 ml |
| | Methylene chloride | 0.27 ml | 0.27 ml | 0.27 ml |
| Coloring agent | Yellow No. 4/ Red No. 40 | q.s | q.s | q.s |
| | Weight of Tablet | 520.4 mg | 524.1 mg | 559.6 mg |

(Pretreatment of Major Herbal Medicines and Their Manufacturing Methods for Formulation)

1. Manufacturing process for Shinseng Radix extract
   1) Method 1
      ① Shinseng Radix is pulverized and powdered, and with the addition of 8-fold amount of 75% ethanol the mixture is extracted under reflux for 2 hours.
      ② The extract is washed with chloroform two times (extract:chloroform=1:1).
      ③ Water layer is extracted with n-butanol (1:1) three times.
      ④ n-Butanol layer is separated and dried under reduced pressure at less than 80° C.
      ⑤ The dried material is powdered.
   2) Method 2
      ① Shinseng Radix is pulverized and powdered, and with the addition of 5-fold amount of 35% ethanol the mixture is extracted under reflux for 2 hours.
      ② 5-fold amount of 35% ethanol is added to the sample and re-extracted under reflux for 2 hours.
      ③ The extract is collected and filtered off.
      ④ The filtered material is dried under reduced pressure at less than 80° C. and powdered.
   3) Method 3
      ① Shinseng Radix is pulverized and powdered, and with the addition of 8-fold amount of water the mixture is extracted under heating for 3 hours.
      ② The extract is left overnight and filtered off.
      ③ The extract is dried under reduced pressure and powdered.

2. Manufacturing process for Coptis Rhizoma extract
   1) Method 1
      ① After being pulverized and powdered, Coptis Rhizoma is added to a 8-fold amount of ethanol and 0.1N hydrochloric acid solution (100:1) and extracted until the yellow color is disappeared using Soxhlet extraction device.
      ② The extracted ethanol-hydrochloric acid solution is evaporated to obtain berberine HCl as a powder form.
   2) Method 2
      ① After being pulverized and powdered, Coptis Rhizoma is added to a 6-fold amount of ethanol and 0.1N hydrochloric acid solution (100:1) and extracted under reflux for 5 hours using a reflux condenser.
      ② The extract is cooled and filtered. Then, the residue is added to a 4-fold amount of ethanol and 0.1N hydrochloric acid solution (100:1) and extracted under reflux for 5 hours using a reflux condenser.
      ③ The extract is re-cooled and filtered off. Then, the residue is added to 4-fold amount of ethanol and 0.1N hydrochloric acid solution (100:1) and extracted under reflux for 5 hours using a reflux condenser.
      ④ After the extract is filtered off, all of collected solution is dried by evaporation to obtain berberine HCl as a powder form.
   3) Method 3
      ① After being pulverized and powdered, Coptis Rhizoma is added to a 8-fold amount of ethanol and water solution (2:1) and extracted under reflux at 60° C. for 12 hours.
      ② The extract is extracted and then, the residue is added to a 4-fold of ethanol and water solution (2:1) and extracted under reflux at 60° C. for 12 hours.

③ After the extract is filtered off, the remaining solution is collected and then, ethanol is distilled under reduced pressure.

④ After 2-fold amount of acetone is added to the water layer of residue and pH is adjusted to 2–3 using a concentrated hydrochloric acid, the remaining solution is left overnight and filtered off.

⑤ The remaining solution is dried at 80° C.

3. Manufacturing process for Ligustri Fructus Semen

1) Method 1

① 4 to 5-fold amount of 95% ethanol is added to well dried fruit of this herb and then, the mixture is extracted for 12 hours. The extract is stored.

② 5-fold amount of n-butanol is added to the sample for 12-hour extraction.

③ The collected extract is fractioned and purified using chromatography column. In this case, the column is filled with silica, and benzene-ether solution (4:1) is used as an eluent.

2) Method 2

① Well dried fruit of this herb is extracted by a 4-fold amount of methanol two times.

② The collected solution is fractioned by a polar solvent for separation and purification.

4. Manufacturing process for Salix spp. Cortex

① The peel of Salix Gilgiana is pulverized, and with the addition of 5-fold amount of ethanol the mixture is stirred at room temperature for 3 hours, followed by extraction and filtration.

② The remaining solution is distilled under reduced pressure to remove ethanol completely. Then, 0.5-fold amount of distilled water in proportion to original herb amount is added to the residue and dissolved by 0.1N NaOH by adjusting pH to 8–9, while filtering off the insoluble material.

③ The remaining solution is cooled and pH is adjusted to 2.0 using 1N HCl. Then, the solution is stirred for 10 minutes and a whitish powder so formed is filtered off and dried under vacuum at 80° C. to obtain salicylic acid as a whitish crystal.

According to this invention, it is preferred to employ salicylic acid or acetylsalicylic acid and its salt, which are purified and separated from dried or extracted Salix spp. Cortex.

5. Processing for *Rhei coreani* Rhizoma

1) Method 1 (pulverization)

The root and trunk of this herb are well dried and then, impurities-free material is placed into a pulverizing machine and finely powdered.

2) Method 2 (extraction)

① *Rhei coreani* Rhizoma is pulverized and powdered and with the addition of 8-fold amount of water, the mixture is heated for 4 hours for extraction.

② The separated extract is concentrated and dried by spraying.

6. Extraction method for other herbs

① All of other herbs are pulverized and powdered, and with the addition of 8-fold amount of water the mixture is heated for 4 hours for extraction.

② The separated extract is concentrated and dried by spraying.

7. Drying and granulation process

① All extracts so prepared from the above 1–6 processes are dried at less than 60° C. and dried in a manner that the water content is less than 9%.

② The dried material is stirred in a mixer while spraying 88% ethanol.

③ Vitamins, etc. are blended to the stirred material for homogenous mixing.

8. Formulation

Hereafter, the resulting material is granulated by a granulator and dried at less than 60° C. and dried in a manner that the water content is less than 9%.

Then, the final material is prepared in the dosage form of Tablet or capsule in accordance with the manufacturing processes specified in the Korean Pharmacopoeia.

(Stability Test of Capsule Formulation)

1. Product name: DHS123 capsule
2. Test period: Jan. 22 through Aug. 8, 2001
3. Test place and testing personnel 1) Location: Quality Control Department, OO Pharmaceutical Co. in Kyunggi Province 2) Test facility:
   HPLC (WATERS)
   AA (SHIMADZU)
   Chemical scale (METTLER)
   Dissolution testing machine (Fine Machine)

3) Testing personnel: 3 persons including Yoon OO

4. Test specimen

1) Manufacturing date
   LOT NO. DHS123C1 (Jan. 16, 2001)
   LOT NO. DHS123C2 (Jan. 20, 2001)
   LOT NO. DHS 123C3 (Jan. 22, 2001)

2) Specimen: capsule preparation in accordance with Preparation Example 1

5. Storage conditions 1) 40° C., 75% RH, 6 months

2) Room temperature

6. Testing items and methods

1) Testing items
   ① appearance, ② identification, ③ dissolution, ④ contents, ⑤ weight deviation 2) Testing methods
   The specimens, so stored in accordance with the item 5, are collected at the intervals of initial test period, 2 months, 4 months and 6 months. The corresponding test is performed in accordance with specification and testing methods (Korean Pharmacopoeia, in-house standards) of DHS123 capsule as the above item 1).

7. Test results (as shown in the following Tables 1–4):

Under the above storage conditions, DHS123 capsule did not show any marked changes in all of the testing items (appearance, identification, dissolution, contents, and weight deviation). Therefore, it has proven that DHS123 capsule has a better stability in terms of storage conditions and expiration period.

Table 1

Stability test results of DHS123 capsule (40° C., 75% RH, RT)

| Lot No. | Item | Initial period | 2 months | 4 months | 6 months | Room temp., 6 months |
|---|---|---|---|---|---|---|
| DHS123C1 | Appearance | Unusual odor, yellowish-brown granule | Unusual odor, yellowish-brown granule | Unusual odor, yellowish-brown granule | Unusual odor, yellowish-brown granule | Unusual odor, yellowish-brown granule |
| | Identification | Approved | — | — | Approved | Approved |
| | Dissolution | Approved | — | — | Approved | Approved |
| | Weight deviation | Approved | — | — | Approved | Approved |
| | Contents (%) | 103.21 | 101.58 | 96.70 | 99.12 | 99.40 |
| | | 115.32 | 116.52 | 127.36 | 117.86 | 124.28 |
| DHS123C2 | Appearance | Unusual odor, yellowish-brown granule | Unusual odor, yellowish-brown granule | Unusual odor, yellowish-brown granule | Unusual odor, yellowish-brown granule | Unusual odor, yellowish-brown granule |
| | Identification | Approved | — | — | Approved | Approved |
| | Dissolution | Approved | — | — | Approved | Approved |
| | Weight deviation | Approved | — | — | Approved | Approved |
| | Contents (%) | 101.61 | 103.76 | 101.38 | 100.42 | 97.46 |
| | | 142.52 | 139.57 | 147.88 | 144.83 | 143.10 |
| DHS123C3 | Appearance | Unusual odor, yellowish-brown granule | Unusual odor, yellowish-brown granule | Unusual odor, yellowish-brown granule | Unusual odor, yellowish-brown granule | Unusual odor, yellowish-brown granule |
| | Identification | Approved | — | — | Approved | Approved |
| | Dissolution | Approved | — | — | Approved | Approved |
| | Weight deviation | Approved | — | — | Approved | Approved |
| | Contents (%) | 103.16 | 99.56 | 97.58 | 100.19 | 97.09 |
| | | 147.59 | 141.61 | 148.33 | 148.18 | 138.72 |

TABLE 2

Test results of DHS123 capsule by lot No. (DHS123C1)

| Item | | Initial period | Accelerated, 2 months | Accelerated, 4 months | Accelerated, 6 months | RT, 6 months |
|---|---|---|---|---|---|---|
| Appearance | | Unusual odor, yellowish-brown granule | Unusual odor, yellowish-brown granule | Unusual odor, yellowish-brown granule | Unusual odor, yellowish-brown granule | Unusual odor, yellowish-brown granule |
| Identification | Coptis Rhizoma | Approved | Approved | Approved | Approved | Approved |
| | Shinseng Radix | Approved | Approved | Approved | Approved | Approved |
| | Ligustri Fructus Seme | Approved | Approved | Approved | Approved | Approved |
| | Salix spp. Cortex | Approved | Approved | Approved | Approved | Approved |
| | *Rhei Coreani* Rhizoma | Approved | Approved | Approved | Approved | Approved |
| | Anemarrhena Rhizoma | Approved | Approved | Approved | Approved | Approved |
| | Salviae Radix | Approved | Approved | Approved | Approved | Approved |
| | Scrophulariae Radix | Approved | Approved | Approved | Approved | Approved |
| | Lycii Cortex Radicis | Approved | Approved | Approved | Approved | Approved |
| | Reynoutriae Radix | Approved | Approved | Approved | Approved | Approved |
| | Platycodi Radix | Approved | Approved | Approved | Approved | Approved |
| | Astragali Radix | Approved | Approved | Approved | Approved | Approved |
| | Puerariae Radix | Approved | Approved | Approved | Approved | Approved |
| | Atractylis Rhizoma | Approved | Approved | Approved | Approved | Approved |
| | *Morus alba* Radix Cortex | Approved | Approved | Approved | Approved | Approved |
| | Thiamine HCl | Approved | Approved | Approved | Approved | Approved |
| | Pyridoxine HCl | Approved | Approved | Approved | Approved | Approved |
| | Zinc | Approved | Approved | Approved | Approved | Approved |
| | Manganese | Approved | Approved | Approved | Approved | Approved |

TABLE 2-continued

Test results of DHS123 capsule by lot No. (DHS123C1)

| Item | | Initial period | Accelerated, 2 months | Accelerated, 4 months | Accelerated, 6 months | RT, 6 months |
|---|---|---|---|---|---|---|
| | Chromium | Approved | Approved | Approved | Approved | Approved |
| Dissolution | | 12 min. 28 sec. | — | — | 12 min. 35 sec. | 12 min. 32 sec. |
| Weight deviation | | Approved | — | — | Approved | Approved |
| Contents | Berberine (%) | 103.21 | 101.58 | 96.70 | 99.12 | 99.40 |
| | Ginsenoside Rb1 (%) | 115.32 | 116.52 | 127.36 | 117.86 | 124.28 |
| | Thiamine HCl (mg/cap.) | 3.34 | 3.49 | 3.16 | 2.97 | 3.71 |
| | Pyridoxine HCl (mg/cap.) | 4.35 | 4.41 | 4.27 | 4.79 | 3.95 |
| | Manganese (mg/cap.) | 1.45 | 1.49 | 1.48 | 1.49 | 1.49 |
| | Zinc (mg/cap.) | 1.31 | 1.28 | 1.30 | 1.32 | 1.30 |

TABLE 3

Test results of DHS123 capsule by lot No. (DHS123C3)

| Item | | Initial period | Accelerated, 2 months | Accelerated, 4 months | Accelerated, 6 months | RT, 6 months |
|---|---|---|---|---|---|---|
| Appearance | | Unusual odor, yellowish-brown granule | Unusual odor, yellowish-brown granule | Unusual odor, yellowish-brown granule | Unusual odor, yellowish-brown granule | Unusual odor, yellowish-brown granule |
| Identification | Coptis Rhizoma | Approved | Approved | Approved | Approved | Approved |
| | Shinseng Radix | Approved | Approved | Approved | Approved | Approved |
| | Ligustri Fructus Semen | Approved | Approved | Approved | Approved | Approved |
| | Salix spp. Cortex | Approved | Approved | Approved | Approved | Approved |
| | *Rhei Coreani* Rhizoma | Approved | Approved | Approved | Approved | Approved |
| | Anemarrhena Rhizoma | Approved | Approved | Approved | Approved | Approved |
| | Salviae Radix | Approved | Approved | Approved | Approved | Approved |
| | Scrophulariae Radix | Approved | Approved | Approved | Approved | Approved |
| | Lycii Cortex Radicis | Approved | Approved | Approved | Approved | Approved |
| | Reynoutriae Radix | Approved | Approved | Approved | Approved | Approved |
| | Platycodi Radix | Approved | Approved | Approved | Approved | Approved |
| | Astragali Radix | Approved | Approved | Approved | Approved | Approved |
| | Puerariae Radix | Approved | Approved | Approved | Approved | Approved |
| | Atractylis Rhizoma | Approved | Approved | Approved | Approved | Approved |
| | *Morus alba* Radix Cortex | Approved | Approved | Approved | Approved | Approved |
| | Thiamine HCl | Approved | Approved | Approved | Approved | Approved |
| | Pyridoxine HCl | Approved | Approved | Approved | Approved | Approved |
| | Zinc | Approved | Approved | Approved | Approved | Approved |
| | Manganese | Approved | Approved | Approved | Approved | Approved |
| | Chromium | Approved | Approved | Approved | Approved | Approved |
| Dissolution | | 12 min. 28 sec. | — | — | 12 min. 35 sec. | 12 min. 32 sec. |
| Weight deviation | | Approved | — | — | Approved | Approved |
| Contents | Berberine (%) | 101.61 | 103.76 | 101.38 | 100.42 | 97.46 |
| | Ginsenoside Rb1 (%) | 142.52 | 139.57 | 147.88 | 144.83 | 143.10 |
| | Thiamine HCl (mg/cap.) | 3.36 | 3.42 | 3.43 | 3.34 | 2.99 |
| | Pyridoxine HCl (mg/cap.) | 4.43 | 4.23 | 4.31 | 4.04 | 4.48 |
| | Manganese (mg/cap.) | 1.46 | 1.52 | 1.51 | 1.48 | 1.48 |

TABLE 3-continued

Test results of DHS123 capsule by lot No. (DHS123C3)

| Item | Initial period | Accelerated, 2 months | Accelerated, 4 months | Accelerated, 6 months | RT, 6 months |
|---|---|---|---|---|---|
| Zinc (mg/cap.) | 1.38 | 1.32 | 1.31 | 1.33 | 1.34 |

TABLE 4

Test results of DHS123 capsule by lot No. (DHS123C3)

| | Item | Initial period | Accelerated, 2 months | Accelerated, 4 months | Accelerated, 6 months | RM, 6 months |
|---|---|---|---|---|---|---|
| | Appearance | Unusual odor, yellowish-brown granule | Unusual odor, yellowish-brown granule | Unusual odor, yellowish-brown granule | Unusual odor, yellowish-brown granule | Unusual odor, yellowish-brown granule |
| Identification | Coptis Rhizoma | Approved | Approved | Approved | Approved | Approved |
| | Shinseng Radix | Approved | Approved | Approved | Approved | Approved |
| | Ligustri Fructus Semen | Approved | Approved | Approved | Approved | Approved |
| | Salix spp. Cortex | Approved | Approved | Approved | Approved | Approved |
| | *Rhei Coreani* Rhizoma | Approved | Approved | Approved | Approved | Approved |
| | Anemarrhena Rhizoma | Approved | Approved | Approved | Approved | Approved |
| | Salviae Radix | Approved | Approved | Approved | Approved | Approved |
| | Scrophulariae Radix | Approved | Approved | Approved | Approved | Approved |
| | Lycii Cortex Radicis | Approved | Approved | Approved | Approved | Approved |
| | Reynoutriae Radix | Approved | Approved | Approved | Approved | Approved |
| | Platycodi Radix | Approved | Approved | Approved | Approved | Approved |
| | Astragali Radix | Approved | Approved | Approved | Approved | Approved |
| | Puerariae Radix | Approved | Approved | Approved | Approved | Approved |
| | Atractylis Rhizoma | Approved | Approved | Approved | Approved | Approved |
| | *Morus alba* Radix Cortex | Approved | Approved | Approved | Approved | Approved |
| | Thiamine HCl | Approved | Approved | Approved | Approved | Approved |
| | Pyridoxine HCl | Approved | Approved | Approved | Approved | Approved |
| | Zinc | Approved | Approved | Approved | Approved | Approved |
| | Manganese | Approved | Approved | Approved | Approved | Approved |
| | Chromium | Approved | Approved | Approved | Approved | Approved |
| | Dissolution | 12 min. 28 sec. | — | — | 12 min. 35 sec. | 12 min. 32 sec. |
| | Weight deviation | Approved | — | — | Approved | Approved |
| Contents | Berberine (%) | 103.16 | 99.56 | 97.58 | 100.19 | 97.09 |
| | Ginsenoside Rb1 (%) | 147.59 | 141.61 | 148.33 | 148.13 | 138.72 |
| | Thiamine HCl (mg/cap.) | 3.50 | 3.09 | 3.11 | 4.02 | 3.24 |
| | Pyridoxine HCl (mg/cap.) | 4.13 | 4.80 | 4.11 | 4.07 | 4.72 |
| | Manganese (mg/cap.) | 1.49 | 1.45 | 1.51 | 1.50 | 1.48 |
| | Zinc (mg/cap.) | 1.35 | 1.35 | 1.30 | 1.32 | 1.34 |

(The Antidiabetic Effect Test)

The antidiabetic effect of the herbal composition of this invention was demonstrated in animal experiments using diabetes-induced mice model, followed by human tests.

To elucidate the glucose-lowering effect of the herbal composition of this invention in animal experiments using ICR mice, the oral glucose tolerance tests were performed. More specifically, KK-Ay mice were used to evaluate the therapeutic effect of the herbal composition of this invention in non-insulin-dependant (type II) diabetes, while streptozotocin-induced mice and NOD mice were used to evaluate the therapeutic effect of the herbal composition of this invention in insulin-dependant (type I) diabetes. In the case of clinical test, the antidiabetic effect of the herbal composition of this invention was measured with respect to the glucose-lowering effect and the improvement of insulin secretion using 118 and 24 non-insulin-dependant diabetics, respectively.

EXPERIMENTAL EXAMPLE 1

OGTT Test in ICR Mice

1) Test Summary

To elucidate the glucose-lowering effect of the specimen of this invention, the oral glucose tolerance test was performed in animal experiments using ICR mice of 5 to 6 weeks in specific pathogen free (SPF), and the glucose-lowering effect between specimen-treated group and control group was compared.

2) Testing Method

A total of 40 animals were selected for this experiment. The animals were divided into 4 groups (each group contains 10 animals) with the following regimen: the first control group (0.85% saline solution), the second control group (dosage in accordance with the Example of Patent Application No. 2001-30134, 10 different herbs containing Shinseng Radix, Coptis Rhizoma, Anemarrhena Rhizoma, Salviae Radix, Lycii Cortex Radicis, Scrophulariae Radix, Reynoutriae Radix, Astragali Radix, Atractylis Rhizoma, and Phellodendri Cortex), the third group (capsule preparation in accordance with the Example of Patent Application No. 2001-3624, 14 different herbs containing Shinseng Radix, Coptis Rhizoma, Ligustri Fructus Semen, Anemarrhena Rhizoma, Salviae Radix, Scrophulariae Radix, Lycii Cortex Radicis, *Rhei coreani* Rhizoma, Reynoutriae Radix, Platycodi Radix, Astragali Radix, Puerariae Radix, Atractylis Rhizoma, and *Morus alba* Radix Cortex), and the fourth group as test group (each capsule preparation is dissolved in 0.85% saline solution, followed by sonification to prepare the suspension for treatment).

The dosage was determined as 13.4 mg/kg based on 60 kg as adult weight, while the dosage of mice was determined as 134 mg/kg, 10-fold amount of human dose.

The specimen was dissolved in 0.85% NaCl solution, followed by sonification to prepare the suspension for treatment. The animals were divided into 10 animals per group and treated with the specimen (0.1 ml) orally every day.

3) Measurement Method

After being fasted for 24 hours, ICR mice were received the specimen and 1 hour after administration, D-(+)-glucose was administered to the animals at the dose of 2 g/kg (0.1 ml per body weight of 10 g). After the blood sample was collected from eyeball, the glucose level was measured using a glucose indicator (Johnson & Johnson Co.) at the intervals of 0, 10, 30, 60, and 120 minutes.

4) Test Results

The test results were shown in the following Table 5 and FIG. 1. Table 5 shows the mean value and standard deviation by measuring the glucose level 30 minutes after administration of the test sample.

TABLE 5

Mean glucose level and standard deviation of OGTT mice

| Category | Control group 1 | Control group 2 | Control group 3 | Test group |
|---|---|---|---|---|
| Mean glucose level (mg/dl) | 345.1 | 255.8 | 245.3 | 228.9 |
| Standard deviation | 35.8 | 51.7 | 43.6 | 32.1 |

Figure 1:
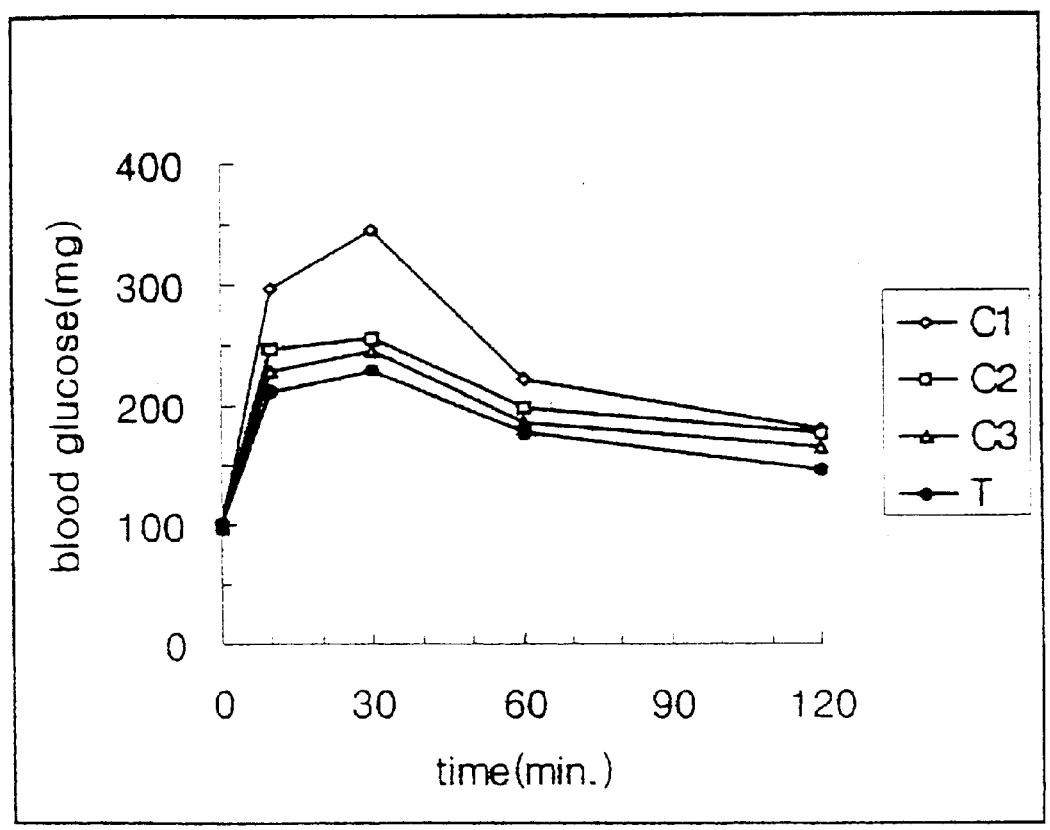

As noted in FIG. 1 and Table 5, the glucose levels of specimen-untreated control group were increased by more than 300 mg/dl 30 minutes after glucose administration, while those of control groups 2 and 3 and test group were lowered by about 100 mg/dl compared to specimen-untreated control group. It revealed that the glucose-lowering effect of test group was higher than those of control groups 2 and 3.

As shown in Table 5, the herbal composition of this invention had relatively small standard deviation among test individuals as well as the glucose-lowering effect, thus suggesting the superiority of equitable therapeutic efficacy.

EXPERIMENTAL EXAMPLE 2

The Glucose-Lowering Effect Test of KK-Ay Mice

1) Test Summary

KK mice are type II diabetes animal models derived from wild mice, which are accompanied by unclear obesity. These animals show insulin resistance and 300~400 mg/dl of glucose level. KK-Ay mice are animal models introducing Ay gene, obesity gene, into KK mice. To evaluate the antidiabetic effect of herbal composition of this invention against non-insulin-dependent (type II) diabetes, the oral glucose tolerance test was performed in this animal experiment using KK-Ay mice, and the glucose-lowering effect was compared.

2) Testing Method

30 KK-Ay mice of 4-weeks were divided into 3 groups (each group contains 10 animals) with the following regimen: the first control group (0.85% saline solution at the dose of 10 ml/kg for daily administration), the second control group (capsule preparation in accordance with the Example of Patent Application No. 2001-3624), and test group (herbal composition of this invention at the dose of 267 mg/10 ml/kg for intraperitoneal administration every day). During the course of 8-week administration, the blood sample was collected from orbital plexusvenosus every week to measure the glucose level. During the administration of test specimen, the body weight of KK-Ay mice was measured to monitor the side effect of herbal composition of this invention.

After termination of drug administration, KK-Ay mice were fasted for 24 hours. The treatment per group schedule was as follows: the first control group (0.85% saline solution), the second control group (capsule preparation in accordance with the Example of Patent Application No. 2001-3624), and test group (herbal composition of this invention in capsule form at the dose of 267 mg/10 ml/kg for intraperitoneal administration). 90 minutes after administration, all mice were orally received glucose at the dose of 1 g/kg. The blood sample was collected from orbital plexusvenosus at the intervals of 30, 45, 60, 90, and 120 minutes to measure the glucose level. The measurement results were indicated as the increased amount of the glucose level from the level before glucose administration.

3) Test Results

Figure 2:
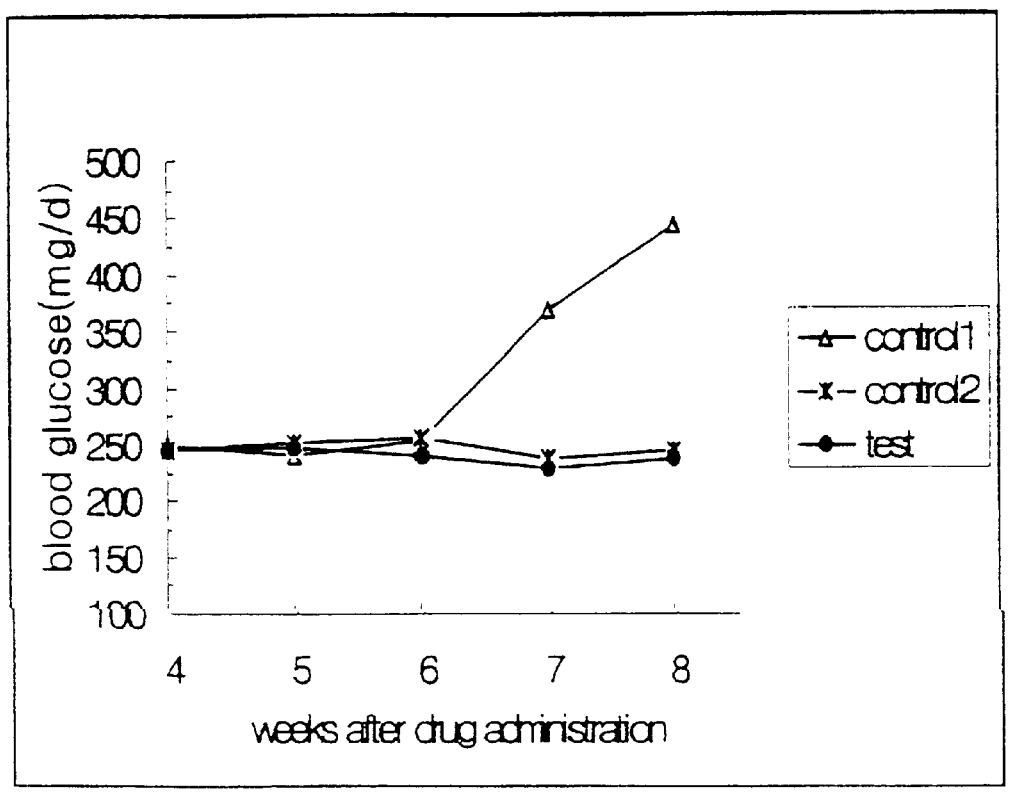
FIG. 2 is a graph showing the antidiabetic effect of the herbal composition of this invention in animal experiments using KK-Ay mice. Animals were administered intraperitoneally the herbal specimen of this invention at the dose of 267 mg/kg every day, while monitoring the changes in glucose level.
Figure 3:
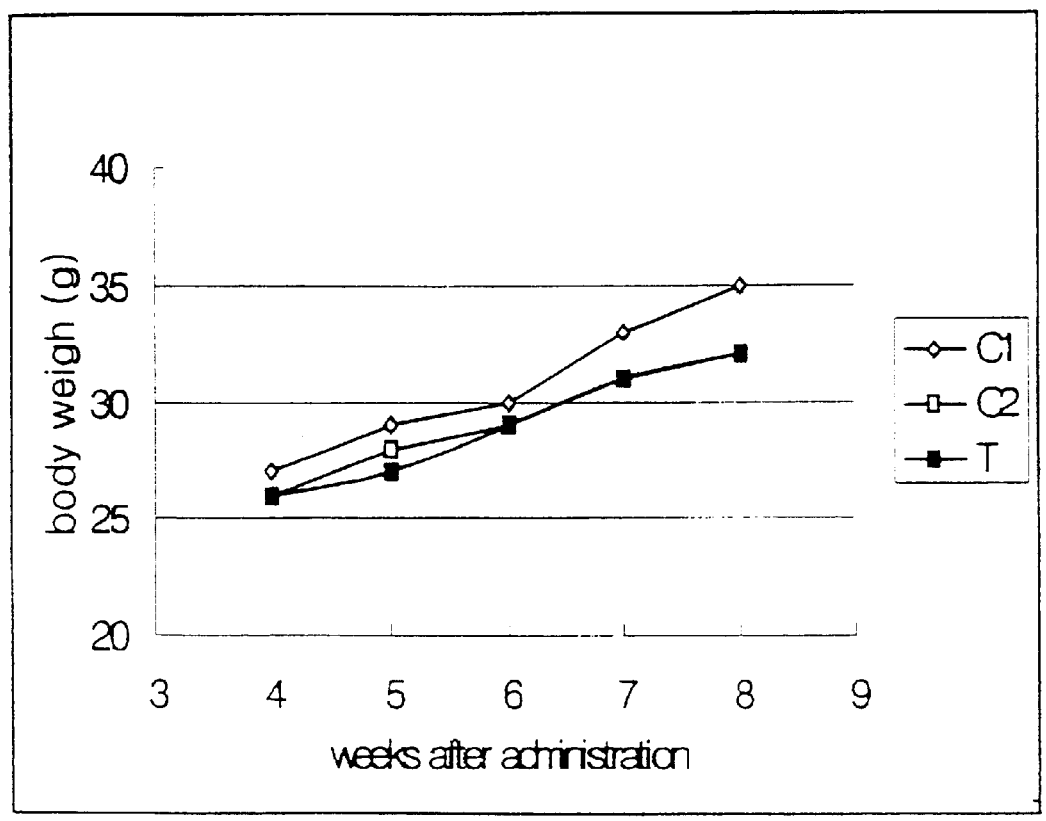
FIG. 3 is a graph showing the changes in body weight of KK-Ay mice in FIG. 2.

The results showing changes of glucose level in KK-Ay mice were shown in FIGS. 2 and 3. The glucose level of the first control group was increased after 6-week administration, thus showing the mean glucose level of more than 400 mg/dl. The second control group and test group revealed the glucose level of 250 mg/dl. The glucose levels of the first control group were increased by 200 mg/dl 30 minutes after glucose adminstration and then decreased slowly, whereas those of the second control group and test group were increased by about 100 mg/dl at the same time interval and then decreased drastically. The corresponding graph has shown that the glucose-lowering effect of herbal composition of this invention was superior to that of the second control group.

During the course of specimen administration for 8 weeks, the body weights of KK-Ay mice were measured to observe the side effects of the specimen and as a result, the test group did not show any weight loss accompanied by the treatment. However, as shown in FIG. 3, the body weights in the second control group and test group were smaller than those of the first control group due to the fact that the weight loss was attributed to antidiabetic treatment in KK-Ay mice, obesity-type diabetic model animals.

EXPERIMENTAL EXAMPLE 3

Test for Streptozotocin-Induced Diabetic Mice
1) Test Summary

Streptozotocin (STZ) was originally developed as antibiotic as N-nitroso derivative of D-glucosamine. STZ has shown to reduce the cellular NAD which leads to the destruction of beta-cell, thus inducing diabetes. With the repeated 5-day administration of STZ to mice at the dose of 60 mg/kg, glucose-dependent diabetes was artificially induced. Then, the specimen was administered to diabetic mice to compare the changes in glucose level and to evaluate the antidiabetic effect of herbal composition of this invention against insulin-dependent diabetes.

2) Testing Method

Experimental animals were supplied from Korea Experimental Animal Center and controlled in an uncontaminated room under the following conditions: temperature (22° C.), humidity (55±5%) and illumination (12L/12D). The experimental animals were divided into 6 groups with the following regimen: the first control group (non-STZ-treated group), the second control group (only STZ-treated group at the dose of 60 mg/kg 3~5 times intraperitoneally), the third control group (STZ+0.85% saline solution as placebo), the fourth group (dosage in accordance with the Example of Patent Application No. 2001-30134, 10 different herbs containing Shinseng Radix, Coptis Rhizoma, Anemarrhena Rhizoma, Salviae Radix, Lycii Cortex Radicis, Scrophulariae Radix, Reynoutriae Radix, Astragali Radix, Atractylis Rhizoma, and Phellodendri Cortex), the fifth group (capsule preparation in accordance with the Example of Patent Application No. 2001-3624, 14 different herbs containing Shinseng Radix, Coptis Rhizoma, Ligustri Fructus Semen, Anemarrhena Rhizoma, Salviae Radix, Scrophulariae Radix, Lycii Cortex Radicis, *Rhei coreani* Rhizoma, Reynoutriae Radix, Platycodi Radix, Astragali Radix, Puerariae Radix, Atractylis Rhizoma, and *Morus alba* Radix Cortex including vitamins $B_1$, $B_6$ and several inorganic materials such as zinc, manganese, chromium, and germanium as test drug), and the test group (in addition to the specimen mentioned in the fifth control group, 26.7 mg of salicylic acid was prepared as capsule preparation of this invention). The corresponding drugs were administered to animals from the initial treatment date to day 23. The changes in body weight, urine glucose, and blood glucose were measured every 4 days.

3) Test Results

Figure 4:
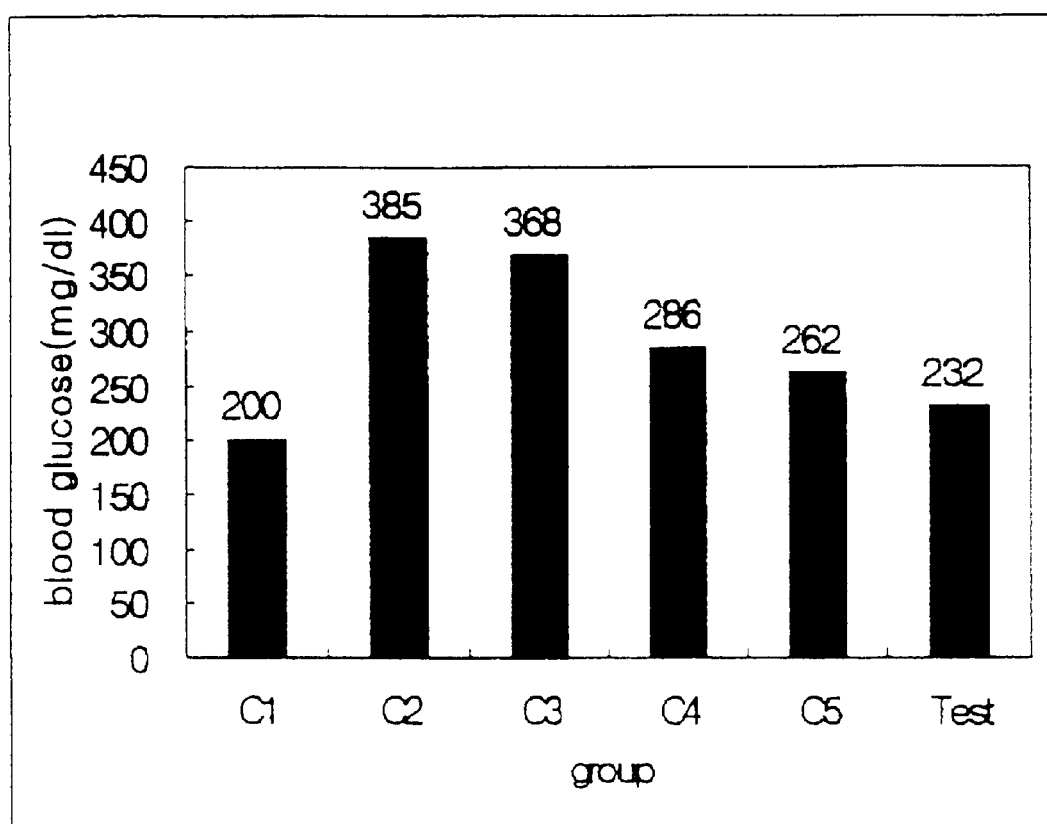
FIGS. 4 and 5 are graphs of the antidiabetic effect of the herbal composition of this invention in animal experiments using streptozotocin-induced diabetic mice. Based on the similar technique, the glucose level of animals was measured every week to evaluate the antidiabetic effect of the herbal composition of this invention.

The measurement results of glucose level among individual animals were shown in the following Table 6. The Table indicated the glucose level of mice and the maximum glucose level was measured up to only 500 mg/dl due to the limitation of measurement technique. FIG. 4 illustrated the mean glucose level per group at day 16 and FIG. 5 was a graph showing the change in mean glucose level per group.

Figure 5:
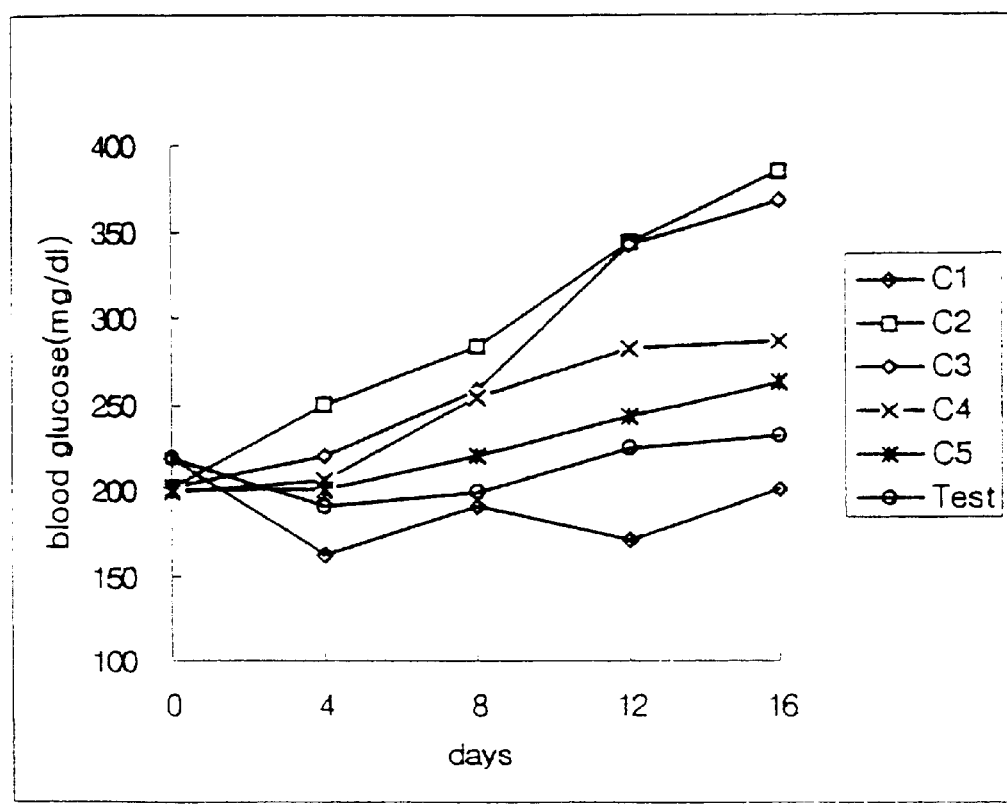

As noted in FIGS. 4 and 5, 10 of 11 animals in the second control group and 10 of 18 in the third control group were judged as diabetic animals, when the glucose level of more than 300 mg/dl was regarded as diabetes. By contrast, significant inhibition effect of diabetes in the forth and fifth control groups and test group was observed; specifically, while there were diabetes in 8 of 18 animals in the forth control group and 4 of 18 animals in the fifth group, only 2 of 18 animals in the test group were judged as diabetic animals.

When the standard deviations among individual animals were compared between the test group and two control groups (4 and 5), the level of standard deviation in the test group was significantly lower than those of the two control groups, thus suggesting better stability of the test sample over those of control groups. Through the above test, it was noted that the occurrence of diabetes in the test group was completely inhibited using the test sample.

TABLE 6

Measured glucose level of STZ mice

| Group | day | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| Control 1 | 0 | 204 | 251 | 200 | 228 | 211 | | | | | | | | | |
| | 4 | 187 | 142 | 150 | 172 | 162 | | | | | | | | | |
| | 8 | 181 | 199 | 178 | 192 | 199 | | | | | | | | | |
| | 12 | 161 | 170 | 176 | 187 | 157 | | | | | | | | | |
| | 16 | 215 | 199 | 190 | 184 | 213 | | | | | | | | | |
| Control 2 | 0 | 208 | 216 | 231 | 192 | 196 | 193 | 181 | 212 | 193 | 193 | 199 | 205 | | |
| | 4 | 295 | 255 | 215 | 308 | | 182 | 244 | 275 | 193 | 226 | 267 | 288 | | |
| | 8 | 325 | 259 | 186 | 500 | | 264 | 485 | 184 | 201 | 195 | 172 | 341 | | |
| | 12 | 394 | 451 | 184 | 500 | | 360 | 474 | 294 | 232 | 217 | 214 | 458 | | |
| | 16 | 406 | 478 | 184 | 500 | | 499 | 500 | 464 | 341 | 186 | 207 | 471 | | |
| Control 3 | 0 | 205 | 204 | 170 | 175 | 199 | 187 | 202 | 190 | 235 | 175 | 216 | 208 | 194 | 188 |
| | 4 | 169 | 261 | 264 | 191 | 203 | 214 | 195 | 168 | 216 | 177 | 289 | 223 | 287 | 168 |
| | 8 | 144 | 228 | 364 | 238 | 314 | 356 | 257 | 148 | 187 | 200 | 280 | 264 | 371 | 179 |
| | 12 | 161 | 406 | 439 | 197 | 490 | 467 | 433 | 193 | 260 | 269 | 488 | 311 | 435 | 347 |
| | 16 | 208 | 468 | 470 | 273 | 500 | 478 | 424 | 230 | 285 | 282 | 500 | 419 | 498 | 408 |
| Control 4 | 0 | 194 | 188 | 217 | 177 | 222 | 206 | 224 | 201 | 207 | 216 | 216 | 187 | 185 | 214 |
| | 4 | 194 | 206 | 152 | 259 | 286 | 174 | 183 | 177 | 176 | 135 | 216 | 338 | 255 | 156 |
| | 8 | 254 | 163 | 166 | 265 | 256 | 252 | 187 | 176 | 202 | 330 | 284 | 496 | 330 | 172 |
| | 12 | 308 | 195 | 180 | 302 | 363 | 250 | 231 | 246 | 300 | 300 | 310 | 500 | 405 | 200 |
| | 16 | 332 | 231 | 153 | 358 | 373 | 217 | 209 | 202 | 257 | 364 | 315 | 500 | 423 | 190 |
| Control 5 | 0 | 197 | 205 | 174 | 171 | 190 | 214 | 168 | 174 | 204 | 212 | 229 | 194 | 218 | 205 |
| | 4 | 148 | 203 | 188 | 192 | 166 | 170 | 181 | 162 | 229 | 167 | 175 | 290 | 195 | 185 |
| | 8 | 182 | 196 | 152 | 197 | 193 | 201 | 188 | 200 | 344 | 216 | 204 | 394 | 203 | 227 |

TABLE 6-continued

Measured glucose level of STZ mice

| | | | | | | | | | | | | | | | | |
|---|---|---|---|---|---|---|---|---|---|---|---|---|---|---|---|---|
| | 12 | 167 | 256 | 166 | 228 | 193 | 220 | 161 | 251 | 426 | 297 | 314 | 500 | 177 | 191 |
| | 16 | 220 | 371 | 210 | 187 | 228 | 203 | 193 | 269 | 431 | 192 | 398 | 469 | 221 | 203 |
| Test | 0 | 221 | 265 | 244 | 245 | 305 | 239 | 231 | 215 | 186 | 171 | 196 | 234 | 197 | 184 |
| group | 4 | 152 | 196 | 197 | 157 | 201 | 187 | 220 | 221 | 191 | 290 | 162 | 182 | 170 | 176 |
| | 8 | 157 | 153 | 188 | 204 | 203 | 166 | 312 | 250 | 107 | 376 | 225 | 186 | 185 | 148 |
| | 12 | 194 | 169 | 181 | 141 | 201 | 215 | 447 | 283 | 214 | 428 | 255 | 189 | 200 | 196 |
| | 16 | 202 | 189 | 220 | 175 | 213 | 242 | 441 | 259 | 201 | 433 | 274 | 189 | 242 | 167 |

| Group | day | 15 | 16 | 17 | 18 | Mean Glucose level | SD |
|---|---|---|---|---|---|---|---|
| Control 1 | 0 | | | | | 218.8 | 20.9 |
| | 4 | | | | | 162.6 | 17.8 |
| | 8 | | | | | 189.8 | 9.9 |
| | 12 | | | | | 170.2 | 12.0 |
| | 16 | | | | | 200.2 | 13.7 |
| Control 2 | 0 | | | | | 201.6 | 13.5 |
| | 4 | | | | | 249.8 | 41.8 |
| | 8 | | | | | 282.9 | 118.3 |
| | 12 | | | | | 343.5 | 119.2 |
| | 16 | | | | | 385.1 | 132.6 |
| Control 3 | 0 | 246 | 211 | 204 | 222 | 201.7 | 20.1 |
| | 4 | 188 | 230 | 192 | 323 | 219.9 | 46.7 |
| | 8 | 234 | 202 | 181 | 500 | 258.2 | 92.8 |
| | 12 | 321 | 253 | 202 | 500 | 342.9 | 116.6 |
| | 16 | 273 | 226 | 182 | 500 | 368.0 | 119.0 |
| Control 4 | 0 | 156 | 185 | 182 | 196 | 198.5 | 18.3 |
| | 4 | 203 | 157 | 191 | 239 | 205.4 | 52.4 |
| | 8 | 277 | 208 | 248 | 302 | 253.8 | 81.2 |
| | 12 | 219 | 211 | 303 | 254 | 282.1 | 81.0 |
| | 16 | 313 | 209 | 268 | 234 | 286.0 | 92.2 |
| Control 5 | 0 | 234 | 200 | 211 | 206 | 200.3 | 19.2 |
| | 4 | 215 | 246 | 221 | 256 | 199.4 | 37.3 |
| | 8 | 222 | 165 | 226 | 245 | 219.7 | 59.2 |
| | 12 | 229 | 173 | 274 | 215 | 241.6 | 91.3 |
| | 16 | 260 | 175 | 252 | 235 | 262.1 | 90.7 |
| Test | 0 | 180 | 199 | 230 | 199 | 218.9 | 34.0 |
| group | 4 | 162 | 194 | 196 | 171 | 190.3 | 31.9 |
| | 8 | 177 | 169 | 209 | 156 | 198.4 | 62.9 |
| | 12 | 165 | 177 | 194 | 182 | 223.9 | 84.1 |
| | 16 | 190 | 162 | 181 | 187 | 231.5 | 81.0 |

EXPERIMENTAL EXAMPLE 4

The Glucose-Lowering Effect Test on NOD

1) Test Summary

NOD mice (non-obese diabetic mice) are insulin-dependent animal models showing the similar type of diabetes with human diabetes naturally from 3~6 months after birth. To evaluate the antidiabetic effect of herbal composition of this invention against insulin-dependent diabetes, the herbal composition of this invention was administered to NOD mice to observe the changes in the glucose level.

2) Testing Method

20 NOD mice ranging from 11 to 20 weeks were selected; 10 animals were assigned to a control group (naturally occurring diabetes) and the other 10 animals were assigned to the test group treated with the test sample at the dose of 134 mg/kg intraperitoneally and then, the changes in glucose level were measured at the intervals of 1 week.

3) Test Results

The following Tables 7 and 8 show the measurement results of glucose level among individual NOD mice belonging to a control and test group. The maximum level was measured up to only 500 mg/dl due to the limitation of measurement technique. Table 9 shows the mean glucose level of the two groups. As shown in the above Tables, the glucose level in the control group was increased from 14-week animals and showed a very high glucose level by more than 400 mg/dl at 20-week animals, while the test group maintained the normal glucose level of 20 mg/dl up to 20-week animals.

FIG. 6 is a graph showing the changes in the glucose level of both control and test groups.

TABLE 7

Measured glucose level of NOD mice-control group

| Week | 1 | 2 | 3 | 4 | 5 | 6 | 7 | 8 | 9 | 10 |
|---|---|---|---|---|---|---|---|---|---|---|
| 9 | 195 | 169 | 204 | 188 | 200 | 165 | 146 | 201 | 175 | 167 |
| 10 | 242 | 165 | 231 | 145 | 209 | 163 | 215 | 197 | 169 | 224 |
| 11 | 207 | 157 | 233 | 159 | 231 | 174 | 201 | 368 | 166 | 214 |

TABLE 7-continued

Measured glucose level of NOD mice-control group

| Week | 1 | 2 | 3 | 4 | 5 | 6 | 7 | 8 | 9 | 10 |
|---|---|---|---|---|---|---|---|---|---|---|
| 12 | 213 | 170 | 310 | 171 | 212 | 183 | 239 | 469 | 200 | 240 |
| 13 | 220 | 166 | 347 | 169 | 230 | 221 | 242 | 480 | 213 | 248 |
| 14 | 244 | 166 | 345 | 170 | 249 | 233 | 244 | 494 | 220 | 382 |
| 15 | 390 | 179 | 360 | 188 | 235 | 269 | 360 | 500 | 230 | 384 |
| 16 | 471 | 184 | 441 | 199 | 213 | 270 | 397 | 500 | 301 | 456 |
| 17 | 493 | 189 | 458 | 220 | 225 | 367 | 402 | 500 | 495 | 490 |
| 18 | 500 | 211 | 500 | 226 | 239 | 480 | 436 | 500 | 495 | 500 |
| 19 | 500 | 176 | 500 | 212 | 237 | 495 | 433 | 500 | 500 | 500 |

TABLE 8

Measured glucose level of NOD mice-test group

| Week | 1 | 2 | 3 | 4 | 5 | 6 | 7 | 8 | 9 | 10 |
|---|---|---|---|---|---|---|---|---|---|---|
| 9 | 179 | 169 | 198 | 143 | 178 | 158 | 275 | 150 | 164 | 190 |
| 10 | 248 | 171 | 154 | 139 | 199 | 212 | 165 | 169 | 175 | 196 |
| 11 | 154 | 204 | 199 | 145 | 430 | 179 | 188 | 194 | 148 | 198 |
| 12 | 192 | 158 | 190 | 165 | 332 | 182 | 221 | 198 | 150 | 200 |
| 13 | 181 | 193 | 149 | 178 | 350 | 162 | 195 | 185 | 147 | 210 |
| 14 | 228 | 145 | 154 | 221 | 309 | 175 | 205 | 177 | 168 | 230 |
| 15 | 209 | 174 | 156 | 199 | 301 | 177 | 169 | 168 | 179 | 215 |
| 16 | 232 | 177 | 202 | 178 | 354 | 198 | 199 | 198 | 161 | 191 |
| 17 | 233 | 151 | 198 | 232 | 400 | 185 | 186 | 180 | 198 | 192 |
| 18 | 215 | 370 | 156 | 219 | 394 | 174 | 264 | 188 | 256 | 179 |
| 19 | 202 | 389 | 167 | 225 | 462 | 204 | 259 | 201 | 270 | 169 |

TABLE 9

Measured mean glucose level of NOD mice

| | Control | Test group |
|---|---|---|
| Glucose level (mg/dl) | 405.3 ± 138.2 | 254.8 ± 97.4 |

EXPERIMENTAL EXAMPLE 5

Destruction of Beta-Cell and its Recovery Test

In the case of insulin-dependent diabetes, the lymphocyte infiltration into pancreatic island of immune cell was observed and this leads to the destruction of beta-cell, thus inducing insulitis. Since macrophage and T-cell is mainly susceptible to infiltration, these immune cells destruct the beta-cell. To evaluate the recovery effect of beta-cell using the herbal composition of this invention, Langerhans island of NOD mice in the pancreas was separated and observed.

In the same manner as Experimental Example 4, NOD mice was divided into two groups, specimen-untreated group and specimen-treated group by herbal composition of this invention. 20 weeks after administration of test samples, pancreases from both groups were separated and fixed with formaline to prepare the tissue specimen. The tissue specimen was stained with hematoxylene/eosine and then, the infiltration of immune cell was measured.

Figure 7A:
Figure 7B:
Figure 7C:
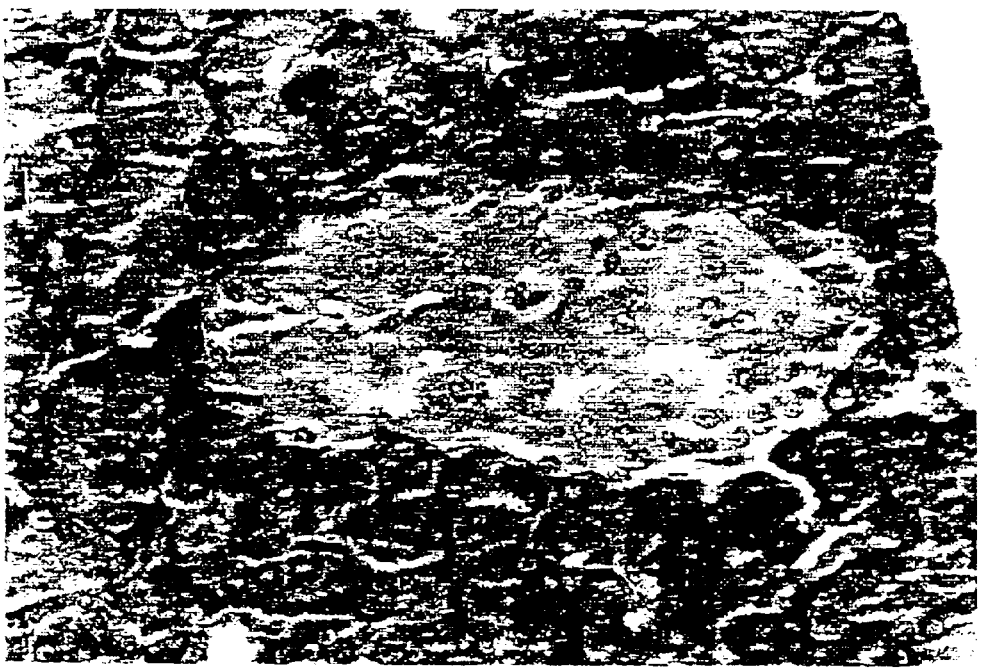
Figure 7D:
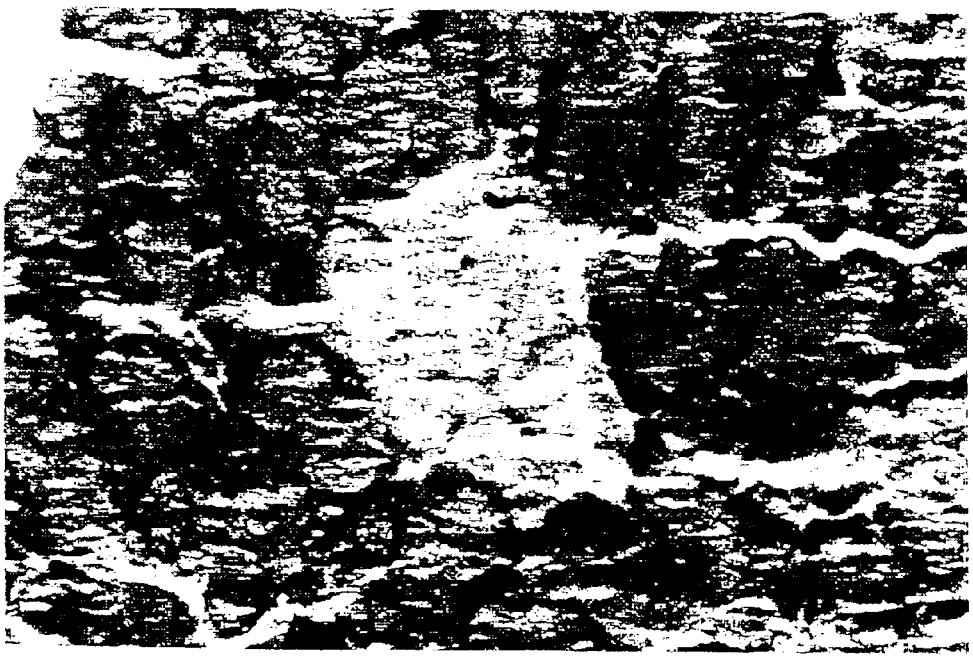

As shown in FIGS. 7a and 7b of the specimen-treated group, there were appearances of little insulitis induced by infiltration of immune cell in the test group, whereas severe infiltration was observed in the untreated control group, as shown in FIGS. 7c and 7d.

From the abovementioned results, the specimen of this invention is effective in inhibiting the infiltration of immune cell and recovery of beta-cell.

CLINICAL EXAMPLE 1

Theapeutic effect on 118 non-insulin-dependent diabetic patients

Test Summary
1. To evaluate the antidiabetic effect of test drug on 118 non-insulin-dependent diabetic patients, the oral glucose tolerance test and insulin release test were performed.
2. Test period: January–September 2001
3. Testing institution: Jasaeing Jungseo Hospital, Changchun city, Jirin Province, China and Jungseo Diabetes Research Center, Bogye city, China.
4. Subjects: 118 diabetic patients who received the continual treatment by more than 60 days among the non-insulin-dependent diabetic in-patients during the above test period.
5. Test drug: Antidiabetic DHS capsule according to this invention (manufactured by OO Pharmaceutical Co.).

Testing Method
1. Selection of subjects
   1) Selection criteria: People falling under one of the following items in accordance with 1998 WHO diagnosis guideline.
   ① Those with the glucose level of more than 7.8 mmol/L (140 mg/dl) on empty stomach when the glucose level in vein is measured; or those with the glucose level of more than 1.0 mmol/L (200 mg/dl) after meals.
   ② Those with the glucose level of more than 11.0 mmol/L (200 mg/dl) as a result of oral glucose tolerance test, even though the glucose level on empty stomach is less than 7.8 mmol/L (140 mg/dl).
   ③ Those who the glucose levels at the intervals of 1 hour and 2 hours after the oral glucose tolerance test are more than 11.0 mmol/L (200 mg/dl), respectively, and the glucose level on empty stomach is 7.8 mmol/L (140 mg/dl).

2) Exclusion criteria: People falling under one of the following items from those who meet the above selection criteria.
① Those with the glucose level of less than 7.8 mmol/L (140 mg/dl) via exercise or diet therapy or with 11.0 mmol/L (200 mg/dl) after 2 hours, even though the glucose level before treatment meets the above selction criteria.
② Those who may affect the calculation of clinical results in violation of test guidelines.
③ Those who are diagnosed as insulin-dependent patients.
④ Those who are diagnosed as diabetic ketosis or acidosis within 1 month from the clinical test.
⑤ Those who have severe complications, psychotropic patients.
⑥ Those who discontinued the treatment or those with false records.
⑦ Those under the age of 15, pregnant or lactating women.

2. Observation method
  1) General observation
    Each individual is observed for general physical examination such as glucose level, including heart, kidney, liver, and blood lipid in some patients.
  2) Measurement of efficacy
    ① The glucose level is measured on empty stomach and 2 hours after meals (measured at the intervals of 10–15 days after the commencement of treatment).
    ② Oral glucose tolerance test.
    ③ Insulin release test.
    ④ Measurement of amino-fructose in the blood.
    From the aforementioned items, ① should be measured and other items may be measured, if deemed necessary. Hereafter, the measurement values before treatment and 60 days after treatment are compared.

3. Administration
  The test drug is orally administered with water 30 minutes before meals, 3 times daily at the dose of 800 mg (2 capsules) once.

4. Judgment criteria
  The following measurement is made in accordance with 'Clinical Research of Diabetes and Guidance Principle' established by Chinese Sanitation Department.
  1) Significant
    With the loss of basic diabetic symptoms after treatment, the glucose level in empty stomach is less than 7.2 mmol/L (130 mg/dl), or the glucose level is less than 8.3 mmol/L (150 mg/dl) 2 hours after meals.
    More than 30% in the glucose level in urine and blood is reduced, when compared with pretreatment.
  2) Effective
    With better improvement of diabetic symptoms after treatment, the glucose level on empty stomach is less than 8.3 mmol/L (150 mg/dl), or the glucose level is less than 10 mol/L (180 mg/dl) 2 hours after meals.
    More than 10% in the glucose level in urine and blood is reduced, when compared with pretreatment.
  3) Ineffective
    With no improvement of diabetic symptoms, the reduction in the glucose level in urine and blood does not meet the aforementioned standard.

Results
1. Glucose-Lowering Effect
  Among a total of 118 non-insulin-dependent diabetic patients, 84 cases (71.25%) were significant, 31 cases (26.3%) were effective, and 3 cases (2.48%) were ineffective. Thus, a total effectiveness was 97.5%.
  The changes in the glucose level of 118 subjects were shown in Tables 10 and 11.

2. Glucose-Lowering Percentage
  Among 118 subjects, there were 97 cases (82.2%) showing more than 30% of glucose-lowering effect, 18 cases (15.2%) showing more than 10% of glucose-lowering effect, and 3 cases showing no glucose-lowering effect or glucose-increasing effect. There were 15 cases showing the glucose level of more than 7.2 mmol/L (130 mg/L) on empty stomach among those showing more than 30% of glucose-lowering effect and those subjects were judged as effective, not significant.

3. Mean Glucose-Lowering Time
  The mean glucose-lowering time of 118 patients was 26.7 days.

4. Side Effects
  Any marked side effects were not observed but some patients showed stomach swelling and diarrhea during the course of clinical trials. Through the adjustment of the treatment in meals or after meals, treatment was continued with better improvement of symptoms.

TABLE 10

Glucose level before treatment (mmol/L)

| Glucose level | Male | Female | Total |
|---|---|---|---|
| 7.1–8.0 | 3 | 3 | 6 |
| 8.1–9.0 | 5 | 7 | 12 |
| 9.1–10.0 | 4 | 3 | 7 |
| 10.1–11.0 | 5 | 3 | 8 |
| 11.1–12.0 | 6 | 5 | 11 |
| 12.1–13.0 | 4 | 4 | 8 |
| 13.1–14.0 | 3 | 7 | 10 |
| 14.1–15.0 | 5 | 2 | 7 |
| 15.1–16.0 | 4 | 5 | 9 |
| 16.1–17.0 | 2 | 6 | 8 |
| 17.1–18.0 | 3 | 5 | 8 |
| 18.1–19.0 | 4 | 3 | 7 |
| 19.1–20.0 | 2 | 2 | 4 |
| 20.1–21.0 | 3 | 2 | 5 |
| 21.1–22.0 | 2 |  | 2 |
| 22.1–23.0 |  | 1 | 1 |
| 23.1–24.0 | 1 | 1 | 2 |
| 24.1–25.0 |  | 1 | 1 |
| 25.1–26.0 | 1 |  | 1 |
| 26.1–30.0 | 1 |  | 1 |
| Total | 58 | 60 | 118 |

TABLE 11

Glucose level after treatment (mmol/L)

| Glucose-lowering | Male | Female | Total |
|---|---|---|---|
| Ineffective | 1 | 2 | 3 |
| <1.0 | 1 |  | 1 |
| 1.1–2.0 | 1 | 1 | 2 |
| 2.1–3.0 | 1 | 2 | 3 |
| 3.1–4.0 | 5 | 7 | 12 |
| 4.1–5.0 | 6 | 8 | 14 |
| 5.1–6.0 | 7 | 5 | 12 |
| 6.1–7.0 | 9 | 6 | 15 |
| 7.1–8.0 | 7 | 6 | 13 |
| 8.1–9.0 | 6 | 7 | 13 |
| 9.1–10.0 | 4 | 5 | 9 |
| 10.1–11.0 | 1 | 2 | 3 |
| 11.1–12.0 | 2 |  | 2 |
| 12.1–13.0 | 4 | 1 | 5 |
| 13.1–14.0 | 1 | 1 | 2 |

TABLE 11-continued

Glucose level after treatment (mmol/L)

| Glucose-lowering | Male | Female | Total |
|---|---|---|---|
| 14.1–15.0 |  | 1 | 1 |
| 15.1–16.0 |  | 1 | 1 |
| 16.1–17.0 | 1 |  | 1 |
| 17.1–18.0 | 2 | 1 | 3 |
| >18.1 | 1 | 2 | 3 |
| Total | 60 | 58 | 118 |

Through the aforementioned tests, it was revealed that the test drug of this invention has a better glucose-lowering effect than the conventional oral glucose-lowering agents or herbal extracts in the treatment of non-insulin-dependent diabetes, while being safe in the incidence of toxicity or side effects.

CLINICAL EXAMPLE 2

Glucose-Lowering Effect and Insulin Release on Diabetic Patients

Summary

To investigate the antidiabetic effect of herbal composition of this invention against non-insulin-dependent diabetes, 24 non-insulin-dependent diabetic patients were selected and treated with the test drug, then changes in glucose level, insulin secretion, and lipid level in blood were measured before and after treatment. As a result, there was a significant glucose-lowering effect in the non-insulin-dependent diabetic patients with the significant increase in insulin level in blood 1 hour after meals, and there was no marked side effect during the course of this clinical trial.

1. Selection of subjects
   1) Selection criteria:
      ① Those with the glucose level of more than 7.8 mmol/L (140 mg/dl) on empty stomach, when the glucose level in vein is measured; those with the glucose level of more than 11.0 mmol/L (200 mg/dl) after meals.
      ② Those with the glucose level of more than 11.0 mmol/L (200 mg/dl) as a result of oral glucose tolerance test, even though the glucose level on empty stomach is less than 7.8 mmol/L (140 mg/dl).
      ③ The glucose levels at the intervals of 1 hour and 2 hours after the oral glucose tolerance test are more than 11.0 mmol/L(200 mg/dl), respectively, or the glucose level on empty stomach is 7.8 mmol/L (140 mg/dl).
   2) Exclusion criteria: People falling under one of the following items from those who meet the above selection criteria.
      ① Those with the glucose level of less than 7.8 mmol/L (140 mg/dl) via exercise or diet therapy or with 11.0 mmol/L (200 mg/dl) after 2 hours, even though the glucose level before treatment meets the above selection criteria.
      ② Those who may affect the calculation of clinical results in violation of test guidelines.
      ③ Those who are diagnosed as insulin-dependent patients.
      ④ Those who are diagnosed as diabetic ketosis or acidosis within 1 month from the clinical test.
      ⑤ Those who have severe complications, psychotropic patients.
      ⑥ Those who discontinued the treatment or those with false records.
      ⑦ Those under the age of 15, pregnant or lactating women.

2. Subject profile

TABLE 12

Target patients

| Sex | | Mean Age | Medical history | Complications | | | |
|---|---|---|---|---|---|---|---|
| Male | Female | | | Hyper-tension | Angina pectoris | Vision | Others |
| 13 | 11 | 56.3 years old | 3–14 years | 6 | 2 | 1 | 4 |

Testing Method

1. Test drug
   1) Name of specimen: DHS capsule (manufactured by OO Pharmaceutical Co.)
   2) Composition of specimen: 1 capsule (400 mg) of this invention contains 15 herbal extracts including vitamins $B_1$, $B_6$ and several inorganic materials.

2. Administration

The test drug is administered three times daily 30 minutes before meals at the dose of 4~6 capsules once. The dosage may be adjusted according to the severity of symptoms.

3. Measurement method
   1) Administration period: The treatment cycle was determined as 60 days after treatment.
   2) Measurement period: The glucose level was measured every week during the course of treatment. The glucose level on empty stomach and the insulin level on empty stomach and 1 hour and 2 hours after meals were measured before treatment and 60 days after treatment.
   3) Measurement equipments: The glucose level was measured using one-touch glucose detector (Johnson & Johnson Co., U.S.A.), and insulin level was also measured using FJ-2008 type preimmune coefficient measurement set (manufactured by Shanhai Factory No. 505).
   4) Administration method: 12 subjects each were assigned to both test group and control group. The test group was received the test sample, while the control group was orally received BBM (marketed product).
   5) Measurment method: All observations such as symptoms, blood pressure and body weight before and after treatment was measured. Other observations such as glucose levels in blood and urine, insulin level in blood, cholesterol (TC) and triglyceride (TG) were measured by enzyme method on empty stomach and 2 hours after meals.
   6) Statistical analysis: All test results were indicated as X+S, while the differences between two groups as $X^2$.

Results

1. Judgment criteria
   1) Satisfactory
      With the loss of basic diabetic symptoms after treatment, the glucose level on empty stomach is less than 7.2 mmol/L(130 mg/dl), and the glucose level is less than 8.3 mmol/L(150 mg/dl) 2 hours after meals. More than 30% in the glucose level in urine and blood is reduced, when compared with pretreatment.

2) Effective

With better improvement of diabetic symptoms after treatment, the glucose level on empty stomach is less than 8.3 mmol/L (150 mg/dl), the glucose level is less than 10 mol/L (180 mg/dl) 2 hours after meals. More than 10% in the glucose level in urine and blood is reduced, when compared with pretreatment.

2. Therapeutic effect

The glucose levels in both groups were significantly reduced ($P<0.01$). From the test group (12 cases), 7 cases were satisfactory and 4 cases were effective, while the control group showed that 4 cases were satisfactory and 4 cases were effective. Thus, a total effectiveness was 91.67% vs. 66.67%, thus suggesting more significant glucose-lowering effect in the test group. The blood-lowering elapse time between the test group and control group were 14.11 days and 26.93 days, respectively, thus demonstrating better therapeutic effect of the test drug.

TABLE 13

Comparison of glucose-lowering effect ($X \pm S$)

| Group | | Case | Glucose level on empty stomach (mmol/L) | Period (day) | Effectiveness |
|---|---|---|---|---|---|
| Test | Before treatment | 12 | 13.11 ± 2.71 | 14.1 ± 2.50 | 91.67% |
|  | After treatment | 12 | 7.26 ± 1.42 | | |
| Control | Before treatment | 12 | 12.98 ± 2.80 | 26.93 ± 12.94 | 66.67% |
|  | After treatment | 12 | 8.62 ± 0.57 | | |

3. Changes in blood insulin

Insulin levels in the test group (12 cases) before and after treatment were measured on empty stomach and 1 hour and 2 hours after meals. There was no significant change between before and after treatment on empty stomach and 2 hours after meals ($p>0.05$). However, insulin levels 1 hour after meals were significantly increased. The results were shown in the following Table 14.

4. Changes in lipid level

TC and TG values were measured before and after treatment. The contents of TC and TG in the observation group were significantly reduced. The results were also shown in the following Table 14.

TABLE 14

Comparison of blood insulin and blood lipid concentration before and after treatment

| | Case | Blood insulin (mmol/L) | | | Blood lipid (mmol/L) | |
| | | Empty stomach | 1 hr. after meals | 2 hr. after meals | TC | TG |
|---|---|---|---|---|---|---|
| Before treatment | 12 | 10.05 ± 3.98 | 41.55 ± 7.22 | 75.66 ± 14.95 | 6.88 ± 0.69 | 2.81 ± 0.66 |
| After treatment | 12 | 10.78 ± 3.90 | 87.29 ± 3.90 | 97.88 ± 12.15 | 5.12 ± 0.50 | 1.19 ± 0.31 |

5. Improvement of symptoms and side effects

All patients in the test group showed disappearance of the excessive drinking, excessive urination and excessive food intake with better physical strength.

Hypertension (6 cases) and blurred vision (1 case) were recovered to the normal level. In the case of angina pectoris (2 cases), one patient was recovered. From other complications including dermatitis (4 cases), 3 patients were recovered.

There was no significant toxicity, side effect and abnormality in liver and kidney.

The diabetic patients want the recovery to normal function and constitution as healthy people, as well as an adequate controlling of glucose level. According to this test, the test drug of this invention can meet their requirements sufficiently.

CLINICAL EXAMPLE 3

Treatment for Insulin-Dependent Diabetic Patient

Case 1

1) Patient's Profile (Housewife: 58 Years Old)

In 1992, she was suffered from three diabetic symptoms and experienced a weight loss from 68 kg to 61 kg in 2 months. During hospitalization, she was diagnosed as diabetes. With drastic increase in the glucose level in blood (280 mg/dl) and visual loss in 1998, the patient had to be hospitalized for 40 days. After discharge, she was received 20 units of insulin daily and during treatment, her glucose level on empty stomach was 180~200 mg/dl.

2) Administration

With the consent of patient and guardian in May 2001, the specimen was administered to the patient and recommended to take it three times daily 30 minutes before meals at the dose of two capsules once.

After 3-week dosing, her glucose level was improved to 138 mg/dl and insulin was reduced to 15 units. After 1 more week, her glucose level was measured as 140 mg/dl and insulin dosage was reduced by another 5 units. After 6-week dosing, she discontinued insulin regimen. Thereafter, when her glucose level was maintained at 140~180 mg/dl on empty stomach, she was recommended to reduce the dosing amount by one capsule.

As of October 2001, the patient maintained the normal glucose level by taking 3 capsules daily at the dose of 1 capsule once and visual loss was further improved.

Case 2

1) Patient's Profile (Female, b. 1937, 64 Years Old, Formly Middle-School Teacher)

The patient was diagnosed as insulin-dependent diabetic patient from her physical examination 10 years ago. Thereafter, with the regular administration of insulin (three times daily, 10 units once) as an outpatient, the patient showed the mean glucose level of 210~230 mg/dl on empty stomach before treatment of the test drug in January 2001. There was no hospitalization record and complications such as three basic diabetic symptoms, weight loss or diabetic complications were not also observed, but she suffered from rash, itching and hypertrophy at the injection site due to the long-term insulin administration.

2) Administration

With the consent of patient and guardian in May 2001, the specimen was administered to the patient and recommended to take it three times daily 30 minutes before meals at the dose of two capsules once. When her glucose level was maintained at less than 180 mg/dl on empty stomach, the patient was recommended to reduce insulin regimen by every 5 units.

After 5-week dosing of the test drug, her glucose level was reduced to 132~167 mg/dl and as a result of reducing insulin amount by 5 units, the patient discontinued insulin therapy and instead, received the test drug at the dose of 6 capsules daily. Her rash, itching and hypertrophy were significantly improved.

Case 3

1) Patient'; Profile (Male, 46 Years Old, Salaryman)

The patient was suffered from three diabetic symptoms from July–August 2000 and experienced a weight loss from 81 kg to 71 kg. During hospitalization, he was diagnosed as diabetes (insulin-dependent). The patient's glucose level on empty stomach was measured as 240~280 mg. Thereafter, he was hospitalized for 1 week and via insulin tolerance test, received 20 units of insulin two times daily. Despite the continual administration of insulin, his glucose level was not improved (220~270 mg/dl), and he suffered from swelling and hypotension since the initiation of insulin therapy.

2) Administration

With the consent of patient and guardian in January 2001, the specimen was administered to the patient and recommended to take it three times daily 30 minutes before meals at the dose of two capsules once, and insulin therapy was discontinued. Instead, the patient's glucose level was examined more than once daily.

During the initial 8-week period there was no change in his glucose level, but from the 9-week period the patient's glucose level was lowered, and at 11 weeks his glucose level was further reduced to less than 180 mg/dl. Thanks to his continual dosing of test drug, the patient's glucose level is currently maintained at 120~160 mg/dl on empty stomach with the dosing of 6 capsules daily. With the complete loss of three diabetic symptoms, his weight was increased to 76 kg.

Case 4

1. Patient's Profile (Male, 72 Years Old, Formerly Civil Servant)

The patient suffered from diabetes from 50 years of age and despite the longstanding administration of Chinese medicines and glucose-lowering agents, there was no significant improvement in diabetic conditions. He was diagnosed as insulin-dependent diabetic patient at hospital two years ago and 45 units of insulin were administered daily to the patient.

The glucose level on empty stomach was 280~330 mg/dl, and his body weight was reduced from 75 kg at the time of the initial diabetic symptoms to 52 kg at present. With severe complications, he complained much of nail infection and skin ulcer but with little basic diabetic symptoms.

2) Administration

With the consent of patient and guardian in February 2001, the specimen was administered to the patient and recommended to take it three times daily 30 minutes before meals at the dose of two capsules once. When his glucose level was maintained at less than 180 mg/dl on empty stomach, the patient was recommended to reduce insulin regimen by every 5 units.

After 6-week dosing of the test drug, his glucose level was reduced to less than 260 mg/dl and as a result of reducing insulin amount by 5 units, the patient discontinued insulin therapy and instead, received the test drug at the dose of 6 capsules daily. With the complete loss of skin ulcer, nails infection was significantly improved.

Case 5

1) Patient's Profile (Female, 42 Years Old)

Diabetes occurred after delivery in 1985, and thereafter she was received an oral glucose-lowering agent. During her initial hospitalization in 1995 and 1997, insulin therapy was initiated and received 10 units once 3 times daily due to the patient's inability to control the glucose level.

The glucose level on empty stomach was 210~240 mg/dl before treatment of the test drug, but she was required to take eye operation due to the visual loss of left eye and glaucoma. However, the patient's operation was delayed due to a high glucose level. In addition, she showed severe diabetic symptoms.

2) Administration

The patient was recommended, from January 2001, to take the test drug three times daily 30 minutes before meals at the dose of two capsules once, together with insulin. When her glucose level was maintained at less than 180 mg/dl on empty stomach, the patient was recommended to reduce insulin regimen by every 5 units.

After 3-week dosing of the test drug, her glucose level was reduced to 138~178 mg/dl and as a result of reducing insulin regimen, the patient discontinued insulin therapy but her glucose level was maintained at 140 mg/dl and received her glaucoma operation in May 2001. The patient discontinued insulin therapy completely and received the test drug at the dose of 4 capsules daily. Her diabetic symptoms were completely disappeared.

This invention aims to provide the novel antidiabetic composition comprising 1) 15 herbal ingredients (i.e., Shinseng Radix, Coptis Rhizoma, Ligustri Fructus Semen, Salix spp. Cortex, Rhei Coreani Rhizoma, Anemarrhena Rhizoma, Salviae Radix, Scrophulariae Radix, Lycii Cortex Radicis, Reynoutriae Radix, Platycodi Radix, Astragali Radix, Puerariae Radix, Atracylis Rhizoma, and Morus alba Radix Cortex), 2) vitamins such as $B_1$, $B_6$, and 3) zinc, manganese, chromium, germanium as inorganic materials. Further, the composition of this invention is extremely effective for the treatment of both insulin-dependent and non-insulin-dependent diabetes in animal experiments and clinical trials.

What is claimed is:

1. A pharmaceutical composition for the treatment of diabetes, wherein it comprises 1) 400~800 wt. part of Shiseng Radix, 1900~3400 wt. part of Coptis Rhizoma, 50~400 wt. part of Ligustri Fructus Semen, 170~1700 wt. part of Salix spp. Cortex, 50~600 wt. part of Rhei Coreani Rhizoma, Rhizoma, 500~800 wt. part of Anemarrhena Rhizoma, 400~600 wt. part of Salviae Radix, 400~700 wt. part of Scrophulariae Radix, 500~800 wt. part of Lycii Cortex Radicis, 400~600 wt. part of Reynoutriae Radix, 300~500 wt. part of Platycodi Raidx, 900~1300 wt. part of Astragali Radix, 600~800 wt. part of Puerariae Radix, 600~800 wt. part of Atractylis Rhizoma, and 250~450 wt. part of Morus alba Radix Cortex, 2) 0.5~4.0% of vitamin $B_1$ and 0.5~5.0% of vitamin $B_6$ as therapeutically acceptable amounts and 3) zinc, manganese, chromium, and germanium as inorganic materials as therapeutically acceptable amounts.

2. The pharmaceutical composition for the treatment of diabetes, wherein it comprises salicylic acid or its salt instead of Salix spp. Cortex.

* * * * *